(12) United States Patent
Zarlengo et al.

(10) Patent No.: US 11,803,399 B2
(45) Date of Patent: *Oct. 31, 2023

(54) INTERACTIVE VIRTUAL ASSISTANT SYSTEM

(71) Applicant: Happy Money, Inc., Torrance, CA (US)

(72) Inventors: Adam Zarlengo, Irvine, CA (US); Chris Courtney, Venice, CA (US); Michael Tepper, Long Beach, CA (US); Josh Hemsley, Mesa, AZ (US); Ryan Howes, Pasadena, CA (US); Daniel Sinner, Corona del Mar, CA (US); Scott Saunders, Laguna Beach, CA (US)

(73) Assignee: Happy Money, Inc., Torrance, CA (US)

( * ) Notice: Subject to any disclaimer, the term of this patent is extended or adjusted under 35 U.S.C. 154(b) by 358 days.

This patent is subject to a terminal disclaimer.

(21) Appl. No.: 16/888,831

(22) Filed: May 31, 2020

(65) Prior Publication Data

US 2021/0374863 A1 Dec. 2, 2021
US 2023/0205558 A9 Jun. 29, 2023

Related U.S. Application Data

(63) Continuation of application No. 15/983,887, filed on May 18, 2018, now Pat. No. 10,678,570.
(60) Provisional application No. 62/508,370, filed on May 18, 2017.

(51) Int. Cl.
*G06F 9/451* (2018.01)
*G06Q 40/06* (2012.01)
*G06Q 40/02* (2023.01)
*G06F 3/04847* (2022.01)
*A61B 5/16* (2006.01)

(52) U.S. Cl.
CPC ............ *G06F 9/453* (2018.02); *A61B 5/165* (2013.01); *G06F 3/04847* (2013.01); *G06Q 40/02* (2013.01); *G06Q 40/06* (2013.01)

(58) Field of Classification Search
CPC ........ G06Q 40/06; G06Q 40/02; A61B 5/165; G06F 3/04847; G06F 9/453
See application file for complete search history.

(56) References Cited

U.S. PATENT DOCUMENTS

| | | | | |
|---|---|---|---|---|
| 6,334,103 B1 * | 12/2001 | Surace | ................ | H04M 3/4936 704/E13.004 |
| 6,904,408 B1 * | 6/2005 | McCarthy | ............ | A61B 5/6815 705/2 |
| 2002/0029203 A1 * | 3/2002 | Pelland | .................... | G06F 3/011 706/12 |

(Continued)

*Primary Examiner* — Tadesse Hailu
*Assistant Examiner* — Alvaro R Calderon, IV
(74) *Attorney, Agent, or Firm* — Alford Law Group, Inc.; Tobi Clinton

(57) ABSTRACT

A method, computer program product, and computer system for defining, at a computing device, psychometric data for a user. An interactive virtual assistant, selected from a plurality of interactive virtual assistants, may be provided on the computing device based upon, at least in part, the psychometric data defined for the user. The user may be prompted, via the interactive virtual assistant, with one or more options.

18 Claims, 11 Drawing Sheets

(56) References Cited

U.S. PATENT DOCUMENTS

| | | | |
|---|---|---|---|
| 2005/0038697 A1* | 2/2005 | Aaron | G06Q 30/02 705/14.54 |
| 2007/0048706 A1* | 3/2007 | Tan | G09B 7/00 434/236 |
| 2008/0262982 A1* | 10/2008 | Rajkhowa | H04L 12/1818 706/11 |
| 2009/0119588 A1* | 5/2009 | Moore | G06Q 10/109 715/706 |
| 2010/0318425 A1* | 12/2010 | Karanjia | G06Q 30/02 705/14.66 |
| 2011/0251978 A1* | 10/2011 | Davies | G06Q 40/00 705/36 R |
| 2012/0016678 A1* | 1/2012 | Gruber | G10L 13/02 704/E21.001 |
| 2012/0041903 A1* | 2/2012 | Beilby | G06N 3/004 706/11 |
| 2013/0275164 A1* | 10/2013 | Gruber | G10L 15/22 705/5 |
| 2014/0244476 A1* | 8/2014 | Shvarts | G06Q 40/025 705/38 |
| 2014/0309806 A1* | 10/2014 | Ricci | G05D 23/1917 701/1 |
| 2014/0310739 A1* | 10/2014 | Ricci | G06Q 20/321 725/75 |
| 2015/0186156 A1* | 7/2015 | Brown | H04L 51/02 715/706 |
| 2016/0078512 A1* | 3/2016 | Yopp | G06Q 30/0639 705/26.41 |
| 2016/0294739 A1* | 10/2016 | Stoehr | G06Q 30/01 |
| 2017/0039336 A1* | 2/2017 | Bitran | G16H 20/70 |
| 2017/0324867 A1* | 11/2017 | Tamblyn | H04L 65/1093 |
| 2017/0324868 A1* | 11/2017 | Tamblyn | H04L 51/046 |
| 2017/0353404 A1* | 12/2017 | Hodge | H04L 67/12 |
| 2018/0211227 A1* | 7/2018 | Jones | G06Q 10/1053 |
| 2018/0253793 A1* | 9/2018 | Buckwalter | G06Q 40/025 |
| 2018/0336048 A1* | 11/2018 | Zarlengo | G06F 9/453 |
| 2020/0065857 A1* | 2/2020 | Lagi | G06F 16/9538 |

\* cited by examiner

10

| | | | | | | | |
|---|---|---|---|---|---|---|---|
| 1. Extraverted, enthusiastic | Disagree strongly ○ | Disagree moderately ○ | Disagree a little ○ | Neither agree nor disagree ○ | Agree a little ○ | Agree moderately ○ | Agree strongly ○ |
| 2. Critical, quarrelsome | Disagree strongly ○ | Disagree moderately ○ | Disagree a little ○ | Neither agree nor disagree ○ | Agree a little ○ | Agree moderately ○ | Agree strongly ○ |
| 3. Dependable, Self-disciplined | Disagree strongly ○ | Disagree moderately ○ | Disagree a little ○ | Neither agree nor disagree ○ | Agree a little ○ | Agree moderately ○ | Agree strongly ○ |
| 4. Anxious, Easily upset | Disagree strongly ○ | Disagree moderately ○ | Disagree a little ○ | Neither agree nor disagree ○ | Agree a little ○ | Agree moderately ○ | Agree strongly ○ |
| 5. Open to new experiences, complex | Disagree strongly ○ | Disagree moderately ○ | Disagree a little ○ | Neither agree nor disagree ○ | Agree a little ○ | Agree moderately ○ | Agree strongly ○ |
| 6. Reserved, quiet | Disagree strongly ○ | Disagree moderately ○ | Disagree a little ○ | Neither agree nor disagree ○ | Agree a little ○ | Agree moderately ○ | Agree strongly ○ |
| 7. Sympathetic, warm | Disagree strongly ○ | Disagree moderately ○ | Disagree a little ○ | Neither agree nor disagree ○ | Agree a little ○ | Agree moderately ○ | Agree strongly ○ |
| 8. Disorganized, careless | Disagree strongly ○ | Disagree moderately ○ | Disagree a little ○ | Neither agree nor disagree ○ | Agree a little ○ | Agree moderately ○ | Agree strongly ○ |
| 9. Calm, Emotionally stable | Disagree strongly ○ | Disagree moderately ○ | Disagree a little ○ | Neither agree nor disagree ○ | Agree a little ○ | Agree moderately ○ | Agree strongly ○ |
| 10. Conventional, uncreative | Disagree strongly ○ | Disagree moderately ○ | Disagree a little ○ | Neither agree nor disagree ○ | Agree a little ○ | Agree moderately ○ | Agree strongly ○ |

FIG. 9

PTSD CheckList – Civilian Version (PCL-C)

Client's Name: _____

Instruction to patient: Below is a list of problems and complaints that veterans sometimes have in response to stressful life experiences. Please read each one carefully, put an "X" in the box to indicate how much you have been bothered by that problem in the last month.

| No. | Response | Not at all (1) | A little bit (2) | Moderately (3) | Quite a bit (4) | Extremely (5) |
|---|---|---|---|---|---|---|
| 1. | Repeated, disturbing memories, thoughts, or images of a stressful experience from the past? | | | | | |
| 2. | Repeated, disturbing dreams of a stressful experience from the past? | | | | | |
| 3. | Suddenly acting or feeling as if a stressful experience were happening again (as if you were reliving it)? | | | | | |
| 4. | Feeling very upset when something reminded you of a stressful experience from the past? | | | | | |
| 5. | Having physical reactions (e.g., heart pounding, trouble breathing, or sweating) when something reminded you of a stressful experience from the past? | | | | | |
| 6. | Avoid thinking about or talking about a stressful experience from the past or avoid having feelings related to it? | | | | | |
| 7. | Avoid activities or situations because they remind you of a stressful experience from the past? | | | | | |
| 8. | Trouble remembering important parts of a stressful experience from the past? | | | | | |
| 9. | Loss of interest in things that you used to enjoy? | | | | | |
| 10. | Feeling distant or cut off from other people? | | | | | |
| 11. | Feeling emotionally numb or being unable to have loving feelings for those close to you? | | | | | |
| 12. | Feeling as if your future will somehow be cut short? | | | | | |
| 13. | Trouble falling or staying asleep? | | | | | |
| 14. | Feeling irritable or having angry outbursts? | | | | | |
| 15. | Having difficulty concentrating? | | | | | |
| 16. | Being "super alert" or watchful on guard? | | | | | |
| 17. | Feeling jumpy or easily startled? | | | | | |

PCL-M for DSM-IV (11/1/94) Weathers, Litz, Huska, & Keane National Center for PTSD - Behavioral Science Division This is a Government document in the public domain.

FIG. 10

INTERACTIVE VIRTUAL ASSISTANT SYSTEM

RELATED CASES

This United States (U.S.) patent application is a continuation and claims the benefit of U.S. patent application Ser. No. 15/983,887, titled INTERACTIVE VIRTUAL ASSISTANT SYSTEM AND METHOD filed on 18 May 2018 by inventors Adam Zarlengo et al., now allowed. U.S. patent application Ser. No. 15/983,887 claims the benefit of U.S. Provisional Application No. 62/508,370, filed on 18 May 2017 by inventors Adam Zarlengo et al., the contents of which are all incorporated by reference for all intents and purposes.

BACKGROUND

Virtual assistants are becoming an increasingly common and important part of how users access information. The ability for virtual assistants to understand users and their psychology may improve user interaction and personalization of options and prompts provided by the virtual assistant. Additionally, money causes psychological effects, but how one behaves with money depends on one's psychology. Yet, current interactive financial solutions fail to take psychology into account when prompting users.

BRIEF SUMMARY OF DISCLOSURE

In one example implementation, a method, performed by one or more computing devices, may include but is not limited to defining, at a computing device, psychometric data for a user. An interactive virtual assistant, selected from a plurality of interactive virtual assistants, may be provided on the computing device based upon, at least in part, the psychometric data defined for the user. The user may be prompted, via the interactive virtual assistant, with one or more options.

One or more of the following example features may be included. Defining the psychometric data for the user may include providing one or more interactive graphical psychometric tests in a user interface of the computing device. The one or more interactive graphical psychometric tests may include one or more slidable user interface features configured to move along a continuous scale between two end points representative of a first level of a psychometric trait and a second level of the psychometric trait. A user may be assigned to one or more personality outcomes based upon, at least in part, the one or more interactive graphical psychometric tests provided in the user interface of the computing device. The interactive virtual assistant may be selected from the plurality of interactive virtual assistants for the user based upon, at least in part, the psychometric data defined for the user. Prompting the user, via the interactive virtual assistant, with the one or more options may include one or more of prompting the user to rate one or more financial transactions, prompting the user with one or more financial savings options, and prompting the user with one or more recommendations to help alleviate financial stress. The interactive virtual assistant may be configured to prompt the user with the one or more financial options via an interactive electronic communication session displayed in a user interface of the computing device.

In another example implementation, a computing system may include one or more processors and one or more memories configured to perform operations that may include but are not limited to defining psychometric data for a user. An interactive virtual assistant, selected from a plurality of interactive virtual assistants, may be provided on the computing device based upon, at least in part, the psychometric data defined for the user. The user may be prompted, via the interactive virtual assistant, with one or more options.

One or more of the following example features may be included. Defining the psychometric data for the user may include providing one or more interactive graphical psychometric tests in a user interface of the computing device. The one or more interactive graphical psychometric tests may include one or more slidable user interface features configured to move along a continuous scale between two end points representative of a first level of a psychometric trait and a second level of the psychometric trait. A user may be assigned to one or more personality outcomes based upon, at least in part, the one or more interactive graphical psychometric tests provided in the user interface of the computing device. The interactive virtual assistant may be selected from the plurality of interactive virtual assistants for the user based upon, at least in part, the psychometric data defined for the user. Prompting the user, via the interactive virtual assistant, with the one or more options may include one or more of prompting the user to rate one or more financial transactions, prompting the user with one or more financial savings options, and prompting the user with one or more recommendations to help alleviate financial stress. The interactive virtual assistant may be configured to prompt the user with the one or more financial options via an interactive electronic communication session displayed in a user interface of the computing device.

In another example implementation, a computer program product may reside on a computer readable storage medium having a plurality of instructions stored thereon which, when executed across one or more processors, may cause at least a portion of the one or more processors to perform operations that may include but are not limited to defining psychometric data for a user. An interactive virtual assistant, selected from a plurality of interactive virtual assistants, may be provided on the computing device based upon, at least in part, the psychometric data defined for the user. The user may be prompted, via the interactive virtual assistant, with one or more options.

One or more of the following example features may be included. Defining the psychometric data for the user may include providing one or more interactive graphical psychometric tests in a user interface of the computing device. The one or more interactive graphical psychometric tests may include one or more slidable user interface features configured to move along a continuous scale between two end points representative of a first level of a psychometric trait and a second level of the psychometric trait. A user may be assigned to one or more personality outcomes based upon, at least in part, the one or more interactive graphical psychometric tests provided in the user interface of the computing device. The interactive virtual assistant may be selected from the plurality of interactive virtual assistants for the user based upon, at least in part, the psychometric data defined for the user. Prompting the user, via the interactive virtual assistant, with the one or more options may include one or more of prompting the user to rate one or more financial transactions, prompting the user with one or more financial savings options, and prompting the user with one or more recommendations to help alleviate financial stress. The interactive virtual assistant may be configured to prompt the user with the one or more financial options via an interactive electronic communication session displayed in a user interface of the computing device.

The details of one or more example implementations are set forth in the accompanying drawings and the description below. Other possible example features and/or possible example advantages will become apparent from the description, the drawings, and the claims. Some implementations may not have those possible example features and/or possible example advantages, and such possible example features and/or possible example advantages may not necessarily be required of some implementations.

BRIEF DESCRIPTION OF THE DRAWINGS

FIG. 9 is an example diagrammatic view of an example TIPI ten-item questionnaire utilized by an interactive virtual assistant process according to one or more example implementations of the disclosure;

FIG. 10 is an example diagrammatic view of an example PTSD Checklist utilized by an interactive virtual assistant process according to one or more example implementations of the disclosure.

Like reference symbols in the various drawings indicate like elements.

DETAILED DESCRIPTION

Figure 1:
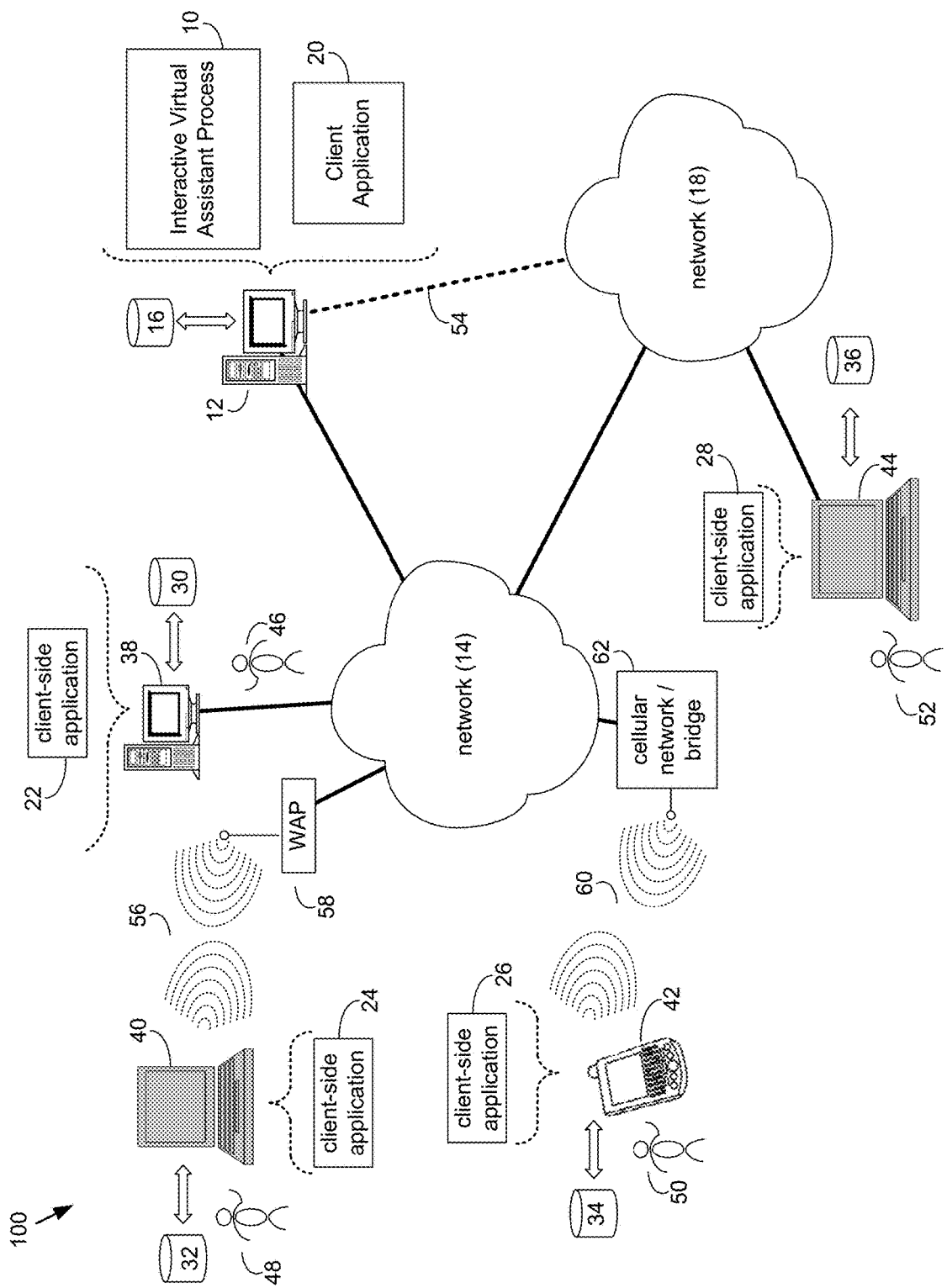
FIG. 1 is an example diagrammatic view of an interactive virtual assistant process coupled to an example distributed computing network according to one or more example implementations of the disclosure.
Figure 2:
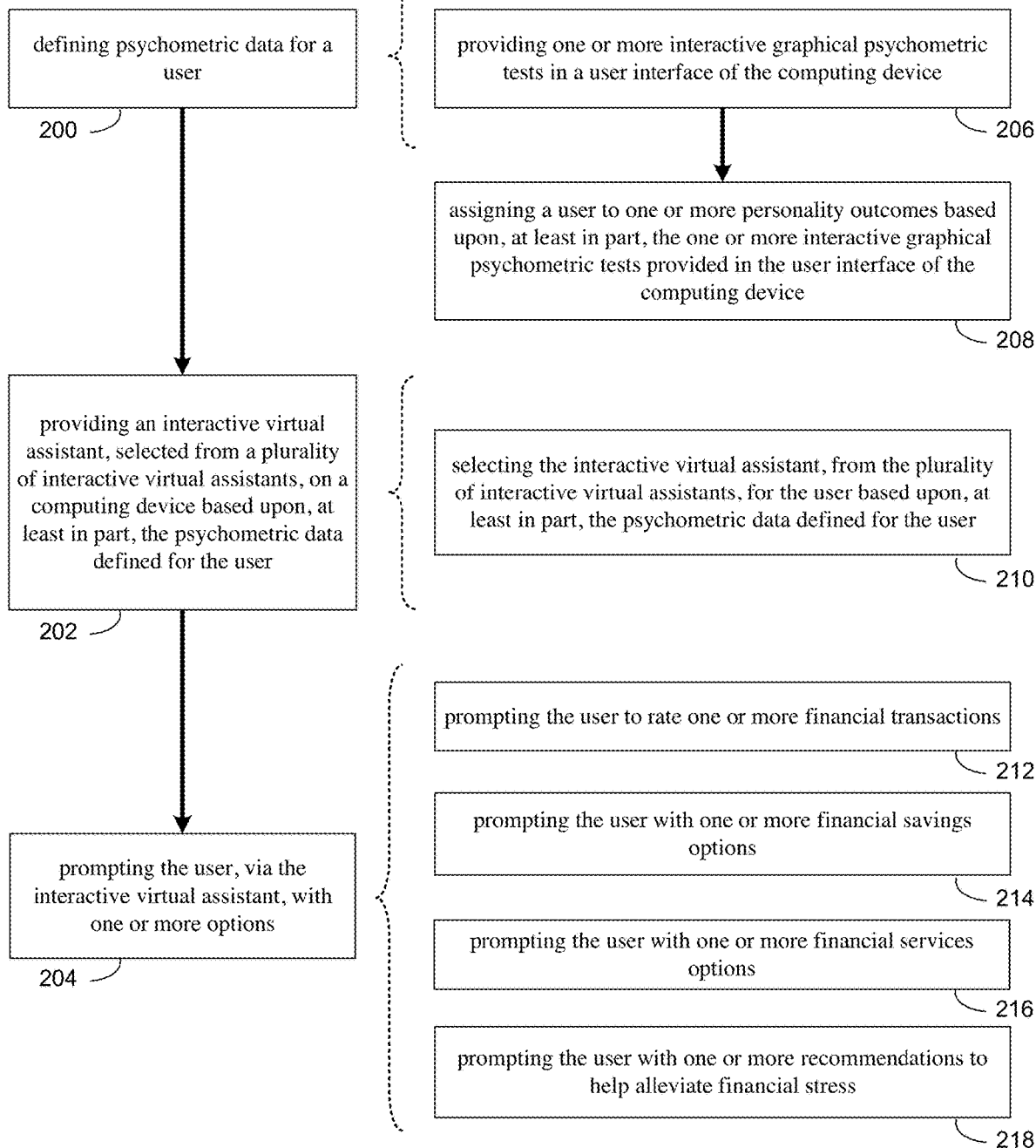
FIG. 2 is an example flowchart of an interactive virtual assistant process according to one or more example implementations of the disclosure.

System Overview:

In some implementations, the present disclosure may be embodied as a method, system, or computer program product. Accordingly, in some implementations, the present disclosure may take the form of an entirely hardware implementation, an entirely software implementation (including firmware, resident software, micro-code, etc.) or an implementation combining software and hardware aspects that may all generally be referred to herein as a "circuit," "module" or "system." Furthermore, in some implementations, the present disclosure may take the form of a computer program product on a computer-usable storage medium having computer-usable program code embodied in the medium.

In some implementations, any suitable computer usable or computer readable medium (or media) may be utilized. The computer readable medium may be a computer readable signal medium or a computer readable storage medium. The computer-usable, or computer-readable, storage medium (including a storage device associated with a computing device or client electronic device) may be, for example, but is not limited to, an electronic, magnetic, optical, electromagnetic, infrared, or semiconductor system, apparatus, device, or any suitable combination of the foregoing. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a digital versatile disk (DVD), a static random access memory (SRAM), a memory stick, a floppy disk, a mechanically encoded device such as punch-cards or raised structures in a groove having instructions recorded thereon, a media such as those supporting the internet or an intranet, or a magnetic storage device. Note that the computer-usable or computer-readable medium could even be a suitable medium upon which the program is stored, scanned, compiled, interpreted, or otherwise processed in a suitable manner, if necessary, and then stored in a computer memory. In the context of the present disclosure, a computer-usable or computer-readable, storage medium may be any tangible medium that can contain or store a program for use by or in connection with the instruction execution system, apparatus, or device.

In some implementations, a computer readable signal medium may include a propagated data signal with computer readable program code embodied therein, for example, in baseband or as part of a carrier wave. In some implementations, such a propagated signal may take any of a variety of forms, including, but not limited to, electromagnetic, optical, or any suitable combination thereof. In some implementations, the computer readable program code may be transmitted using any appropriate medium, including but not limited to the internet, wireline, optical fiber cable, RF, etc. In some implementations, a computer readable signal medium may be any computer readable medium that is not a computer readable storage medium and that can communicate, propagate, or transport a program for use by or in connection with an instruction execution system, apparatus, or device.

In some implementations, computer program code for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java®, Smalltalk, C++ or the like. Java® and all Java-based trademarks and logos are trademarks or registered trademarks of Oracle and/or its affiliates. However, the computer program code for carrying out operations of the present disclosure may also be written in conventional procedural programming languages, such as the "C" programming language, PASCAL, or similar programming languages, as well as in scripting languages such as Javascript, PERL, or Python. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the internet using an Internet Service Provider). In some implementations, electronic circuitry including, for example, programmable logic circuitry, field-programmable gate arrays (FPGAs) or other hardware accelerators, micro-controller units (MCUs), or programmable logic arrays (PLAs) may execute the computer readable program instructions/code by utilizing state information of the computer readable program instructions to personalize the electronic circuitry, in order to perform aspects of the present disclosure.

In some implementations, the flowchart and block diagrams in the figures illustrate the architecture, functionality, and operation of possible implementations of apparatus (systems), methods and computer program products according to various implementations of the present disclosure. Each block in the flowchart and/or block diagrams, and combinations of blocks in the flowchart and/or block diagrams, may represent a module, segment, or portion of code, which comprises one or more executable computer program instructions for implementing the specified logical function(s)/act(s). These computer program instructions may be provided to a processor of a general purpose computer, special purpose computer, or other programmable data processing apparatus to produce a machine, such that the computer program instructions, which may execute via the processor of the computer or other programmable data processing apparatus, create the ability to implement one or more of the functions/acts specified in the flowchart and/or block diagram block or blocks or combinations thereof. It should be noted that, in some implementations, the functions noted in the block(s) may occur out of the order noted in the figures (or combined or omitted). For example, two blocks shown in succession may, in fact, be executed substantially concurrently, or the blocks may sometimes be executed in the reverse order, depending upon the functionality involved.

In some implementations, these computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks or combinations thereof.

In some implementations, the computer program instructions may also be loaded onto a computer or other programmable data processing apparatus to cause a series of operational steps to be performed (not necessarily in a particular order) on the computer or other programmable apparatus to produce a computer implemented process such that the instructions which execute on the computer or other programmable apparatus provide steps for implementing the functions/acts (not necessarily in a particular order) specified in the flowchart and/or block diagram block or blocks or combinations thereof.

Referring now to the example implementation of FIG. 1, there is shown interactive virtual assistant process 10 that may reside on and may be executed by a computer (e.g., computer 12), which may be connected to a network (e.g., network 14) (e.g., the internet or a local area network). Examples of computer 12 (and/or one or more of the client electronic devices noted below) may include, but are not limited to, a storage system (e.g., a Network Attached Storage (NAS) system, a Storage Area Network (SAN)), a personal computer(s), a laptop computer(s), mobile computing device(s), a server computer, a series of server computers, a mainframe computer(s), or a computing cloud(s). As is known in the art, a SAN may include one or more of the client electronic devices, including a RAID device and a NAS system. In some implementations, each of the aforementioned may be generally described as a computing device. In certain implementations, a computing device may be a physical or virtual device. In many implementations, a computing device may be any device capable of performing operations, such as a dedicated processor, a portion of a processor, a virtual processor, a portion of a virtual processor, portion of a virtual device, or a virtual device. In some implementations, a processor may be a physical processor or a virtual processor. In some implementations, a virtual processor may correspond to one or more parts of one or more physical processors. In some implementations, the instructions/logic may be distributed and executed across one or more processors, virtual or physical, to execute the instructions/logic. Computer 12 may execute an operating system, for example, but not limited to, Microsoft® Windows®; Mac® OS X®; Red Hat® Linux®, Windows® Mobile, Chrome OS, Blackberry OS, Fire OS, or a custom operating system. (Microsoft and Windows are registered trademarks of Microsoft Corporation in the United States, other countries or both; Mac and OS X are registered trademarks of Apple Inc. in the United States, other countries or both; Red Hat is a registered trademark of Red Hat Corporation in the United States, other countries or both; and Linux is a registered trademark of Linus Torvalds in the United States, other countries or both).

In some implementations, as will be discussed below in greater detail, an interactive virtual assistant process, such as interactive virtual assistant process 10 of FIG. 1, may include defining, at a computing device, psychometric data for a user (also referred to herein as a client). An interactive virtual assistant, selected from a plurality of interactive virtual assistants, may be provided on the computing device based upon, at least in part, the psychometric data defined for the user (client). The user may be prompted, via the interactive virtual assistant, with one or more options.

In some implementations, the instruction sets and subroutines of interactive virtual assistant process 10, which may be stored on storage device, such as storage device 16, coupled to computer 12, may be executed by one or more processors and one or more memory architectures included within computer 12. In some implementations, storage device 16 may include but is not limited to: a hard disk drive; all forms of flash memory storage devices; a tape drive; an optical drive; a RAID array (or other array); a random access memory (RAM); a read-only memory (ROM); or combination thereof. In some implementations, storage device 16 may be organized as an extent, an extent pool, a RAID extent (e.g., an example 4D+1P R5, where the RAID extent may include, e.g., five storage device extents that may be allocated from, e.g., five different storage devices), a mapped RAID (e.g., a collection of RAID extents), or combination thereof.

In some implementations, network 14 may be connected to one or more secondary networks (e.g., network 18), examples of which may include but are not limited to: a local area network; a wide area network; or an intranet, for example.

In some implementations, computer 12 may include a data store, such as a database (e.g., relational database, object-oriented database, triplestore database, etc.) and may be located within any suitable memory location, such as storage device 16 coupled to computer 12. In some implementations, data, metadata, information, etc. described throughout the present disclosure may be stored in the data store. In some implementations, computer 12 may utilize any known database management system such as, but not limited to, DB2, in order to provide multi-user access to one or more databases, such as the above noted relational database. In some implementations, the data store may also be a custom database, such as, for example, a flat file database or an XML database. In some implementations, any other form(s) of a data storage structure and/or organization may also be used. In some implementations, interactive virtual assistant process 10 may be a component of the data store, a standalone application that interfaces with the above noted data store and/or an applet/application that is accessed via client applications 22, 24, 26, 28. In some implementations, the above noted data store may be, in whole or in part, distributed in a cloud computing topology. In this way, computer 12 and storage device 16 may refer to multiple devices, which may also be distributed throughout the network.

In some implementations, computer 12 may execute a client application (e.g., client application 20), examples of which may include, but are not limited to, e.g., financial applications, a website application, a banking application, a client application (e.g., client account data, spreadsheets, etc.), or other application that allows for accessing a user's financial information and/or transferring a user's funds (e.g., digital currency, tangible currency, stocks, bonds, interests, etc.). In some implementations, interactive virtual assistant process 10 and/or client application 20 may be accessed via one or more of client applications 22, 24, 26, 28. In some implementations, interactive virtual assistant process 10 may be a standalone application, or may be an applet/application/script/extension that may interact with and/or be executed within client application 20, a component of client application 20, and/or one or more of client applications 22, 24, 26, 28. In some implementations, client application 20 may be a standalone application, or may be an applet/application/script/extension that may interact with and/or be executed within interactive virtual assistant process 10, a component of interactive virtual assistant process 10, and/or one or more of client applications 22, 24, 26, 28. In some implementations, one or more of client applications 22, 24, 26, 28 may be a standalone application, or may be an applet/application/script/extension that may interact with and/or be executed within and/or be a component of interactive virtual assistant process 10 and/or client application 20. Examples of client applications 22, 24, 26, 28 may include, but are not limited to, e.g., financial applications, a website application, a banking application, a client application (e.g., client account data, spreadsheets, etc.), or other application that allows for accessing a user's financial information and/or transferring a user's funds (e.g., digital currency, tangible currency, stocks, bonds, interests, etc., a standard and/or mobile web browser, an email application (e.g., an email client application), a textual and/or a graphical user interface, a customized web browser, a plugin, an Application Programming Interface (API), or a custom application. The instruction sets and subroutines of client applications 22, 24, 26, 28, which may be stored on storage devices 30, 32, 34, 36, coupled to client electronic devices 38, 40, 42, 44, may be executed by one or more processors and one or more memory architectures incorporated into client electronic devices 38, 40, 42, 44.

In some implementations, one or more of storage devices 30, 32, 34, 36, may include but are not limited to: hard disk drives; flash drives, tape drives; optical drives; RAID arrays; random access memories (RAM); and read-only memories (ROM). Examples of client electronic devices 38, 40, 42, 44 (and/or computer 12) may include, but are not limited to, a personal computer (e.g., client electronic device 38), a laptop computer (e.g., client electronic device 40), a smart/data-enabled, cellular phone (e.g., client electronic device 42), a notebook computer (e.g., client electronic device 44), a tablet, a server, a television, a smart television, a media (e.g., video, photo, etc.) capturing device, and a dedicated network device. Client electronic devices 38, 40, 42, 44 may each execute an operating system, examples of which may include but are not limited to, Android™, Apple® iOS®, Mac® OS X®; Red Hat® Linux®, Windows® Mobile, Chrome OS, Blackberry OS, Fire OS, or a custom operating system.

In some implementations, one or more of client applications 22, 24, 26, 28 may be configured to effectuate some or all of the functionality of interactive virtual assistant process 10 (and vice versa). Accordingly, in some implementations, interactive virtual assistant process 10 may be a purely server-side application, a purely client-side application, or a hybrid server-side/client-side application that is cooperatively executed by one or more of client applications 22, 24, 26, 28 and/or interactive virtual assistant process 10.

In some implementations, one or more of client applications 22, 24, 26, 28 may be configured to effectuate some or all of the functionality of client application 20 (and vice versa). Accordingly, in some implementations, client application 20 may be a purely server-side application, a purely client-side application, or a hybrid server-side/client-side application that is cooperatively executed by one or more of client applications 22, 24, 26, 28 and/or client application 20. As one or more of client applications 22, 24, 26, 28, interactive virtual assistant process 10, and client application 20, taken singly or in any combination, may effectuate some or all of the same functionality, any description of effectuating such functionality via one or more of client applications 22, 24, 26, 28, interactive virtual assistant process 10, client application 20, or combination thereof, and any described interaction(s) between one or more of client applications 22, 24, 26, 28, interactive virtual assistant process 10, client application 20, or combination thereof to effectuate such functionality, should be taken as an example only and not to limit the scope of the disclosure.

In some implementations, one or more of users 46, 48, 50, 52 may access computer 12 and interactive virtual assistant process 10 (e.g., using one or more of client electronic devices 38, 40, 42, 44) directly through network 14 or through secondary network 18. Further, computer 12 may be connected to network 14 through secondary network 18, as illustrated with phantom link line 54. Interactive virtual assistant process 10 may include one or more user interfaces, such as browsers and textual or graphical user interfaces, through which users 46, 48, 50, 52 may access interactive virtual assistant process 10.

In some implementations, the various client electronic devices may be directly or indirectly coupled to network 14 (or network 18). For example, client electronic device 38 is shown directly coupled to network 14 via a hardwired network connection. Further, client electronic device 44 is shown directly coupled to network 18 via a hardwired network connection. Client electronic device 40 is shown wirelessly coupled to network 14 via wireless communication channel 56 established between client electronic device 40 and wireless access point (i.e., WAP) 58, which is shown directly coupled to network 14. WAP 58 may be, for example, an IEEE 802.11a, 802.11b, 802.11g, 802.11n, 802.11ac, Wi-Fi®, RFID, and/or Bluetooth™ (including Bluetooth™ Low Energy) device that is capable of establishing wireless communication channel 56 between client electronic device 40 and WAP 58. Client electronic device 42 is shown wirelessly coupled to network 14 via wireless communication channel 60 established between client electronic device 42 and cellular network/bridge 62, which is shown by example directly coupled to network 14.

In some implementations, some or all of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. Bluetooth™ (including Bluetooth™ Low Energy) is a telecommunications industry specification that allows, e.g., mobile phones, computers, smart phones, and other electronic devices to be interconnected using a short-range wireless connection. Other forms of interconnection (e.g., Near Field Communication (NFC)) may also be used.

In some implementations, various I/O requests (e.g., I/O request 15) may be sent from, e.g., client applications 22, 24, 26, 28 to, e.g., computer 12. Examples of I/O request 15 may include but are not limited to, data write requests (e.g., a request that content be written to computer 12) and data read requests (e.g., a request that content be read from computer 12).

As will be discussed below, interactive virtual assistant process 10 may at least help, e.g., improve financial and structured media product technology processes, which are necessarily rooted in computer technology in order to overcome an example and non-limiting problem specifically arising in the realm of machine learning based generation of financial and structured media products). It will be appreciated that the computer processes described throughout are not considered to be well-understood, routine, and conventional functions.

The Interactive Virtual Assistant Process:

As discussed above and referring also at least to the example implementations of FIGS. 2-11, interactive virtual assistant process 10 may define 200, at a computing device, psychometric data for a user. Interactive virtual assistant process 10 may provide 202 an interactive virtual assistant, selected from a plurality of interactive virtual assistants, on the computing device based upon, at least in part, the psychometric data defined for the user. Interactive virtual assistant process 10 may prompt 204 the user, via the interactive virtual assistant, with one or more options.

As will be discussed in greater detail below, interactive virtual assistant process 10 may utilize psychometric data defined for a user to select and provide each user with an interactive virtual assistant that speaks to, encourages, and motivates the user. For example and as will be discussed in greater detail below, interactive virtual assistant process 10 may provide an interactive virtual assistant to the user and prompt the user, via the interactive virtual assistant to rate their financial transactions and may surface the types of transactions that makes the user happiest, the user's trends and habits, where the user can cut back without sacrificing happiness, what types of spending is making their peers happy and where they can shift/modify their spending to increase happiness (i.e. spending less on things that make them sad). In some implementations, interactive virtual assistant process 10 may prompt, via the interactive virtual assistant, the user with financial savings options that provide an easy way for the user to save money each day that requires little change to existing habits. Interactive virtual assistant process 10, via the interactive virtual assistant, may also identify larger savings opportunities (i.e. a personal loan for credit card debt elimination) and may prompt the user with these options in a way that most resonates with their psychological makeup.

In some implementations, interactive virtual assistant process 10 may define 200, at a computing device, psychometric data for a user. Psychometric data may generally include data related to objective measurement of skills and knowledge, abilities, attitudes, personality traits, and educational achievement of an individual. As will be discussed in greater detail below, the ability to effectively and simply define psychometric data for a user may enable interactive virtual assistant process 10 to provide 202 an interactive virtual assistant that matches or is otherwise compatible with the user's personality. In some implementations, interactive virtual assistant process 10 may define psychometric data for a user based upon, at least in part, the Big Five Personality Inventory. The Big Five Personality Inventory may be used to assess individual response levels related to the five core dimensions of personality that may include, e.g., openness, conscientiousness, extraversion, agreeableness, and neuroticism. These dimensions may be core traits that remain largely unchanged throughout an individual's life. Personality traits related to openness may include, e.g., imagination and insight. Personality traits related to conscientiousness may include, e.g., a high level of thoughtfulness, good impulse control, and goal-directed behavior. Personality traits related to extraversion may include, e.g., excitability, sociability, talkativeness, assertiveness, and a high degree of emotional expressiveness. Personality traits related to agreeableness may include, e.g., trust, altruism, kindness, affection, and other pro-social behaviors. Personality traits related to neuroticism may include, e.g., anxiety, moodiness, irritability, and sadness. While the Big Five Personality Inventory has been described, it will be appreciated that other psychometric data, such as different classifications of a user's personality may be define 200 via interactive virtual assistant process 10 within the scope of the present disclosure.

Figure 3:
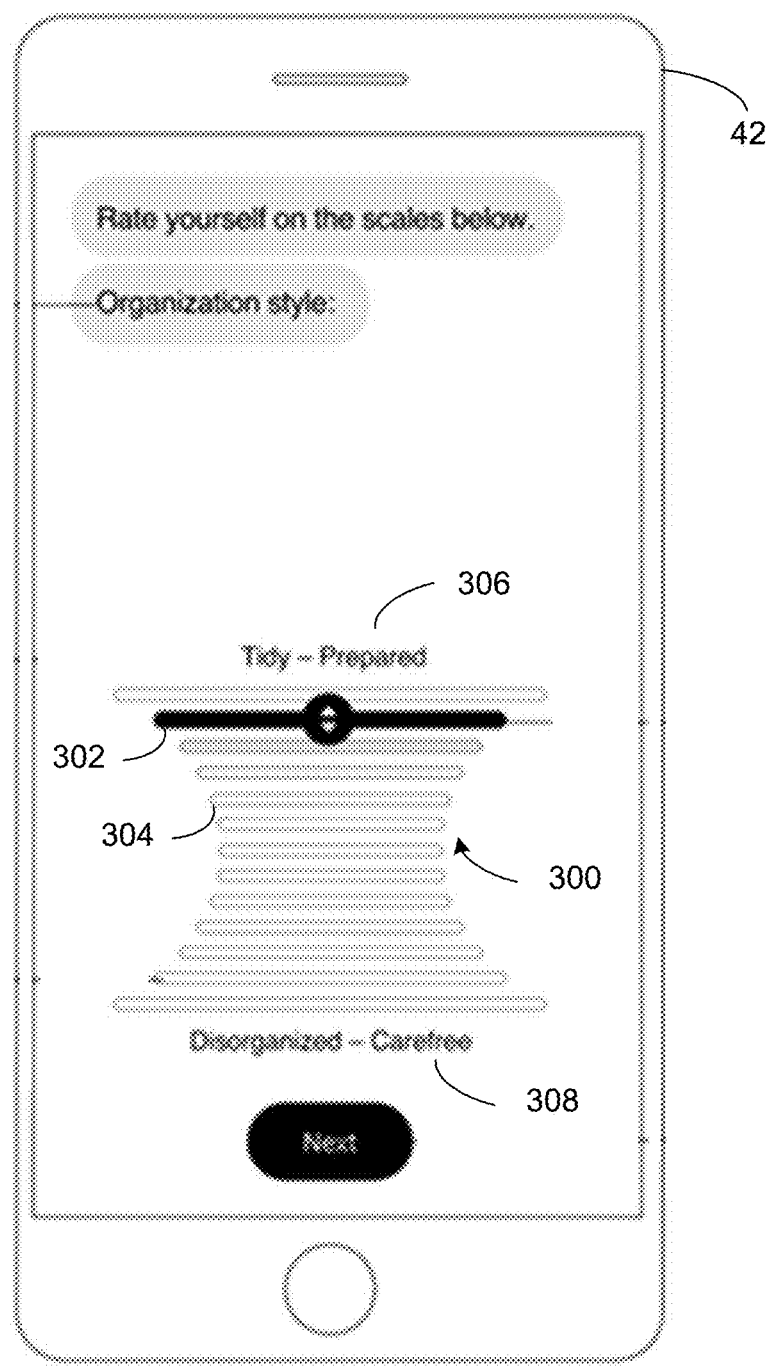
FIG. 3 is an example diagrammatic view of an interactive graphical psychometric test displayed by an interactive virtual assistant process according to one or more example implementations of the disclosure

In some implementations and referring also to FIG. 3, defining 200 the psychometric data for the user may include providing 206 one or more interactive graphical psychometric tests in a user interface of the computing device. As shown in FIG. 3, interactive virtual assistant process 10 may provide 206 an interactive graphical psychometric test in a user interface of a computing device (e.g., client electronic device 42). While the computing device (e.g., client electronic device 42) is represented as a mobile device, it will be appreciated that any computing device (as described above) may be used within the scope of the present disclosure. Additionally, while a single graphical psychometric test is shown in the user interface of the computing device, multiple graphical psychometric tests are possible and within the scope of the present disclosure. In the example, the graphical psychometric test (e.g., graphical psychometric test 300) is represented in an hourglass shape, where the hourglass may correspond to a characteristic of psychometric data for a user. In some implementations, graphical psychometric test (e.g., graphical psychometric test 300) may correspond to one dimension of the Big Five personality inventory.

In some implementations, the assessment items of the graphical psychometric test (e.g., graphical psychometric test 300) may be based upon the Ten-Item Personality Inventory (TIPI), which was designed to assess the traits defined by the Big Five Personality Inventory. As will be described in greater detail below, the evaluation results derived from users interacting with the graphical psychometric test (e.g., graphical psychometric test 300) may correlate well with the evaluation results derived from the TIPI ten-item questionnaire, as shown in FIG. 9. However, one of the example and non-limiting advantages of using the hourglass shaped items of the graphical psychometric test (e.g., graphical psychometric test 300), as shown in FIG. 3, is that users and their psychometric data may be defined 200 quickly, efficiently, and accurately compared to other personality or psychometric tests. Additionally, the experience provided in the graphical psychometric test (e.g., graphical psychometric test 300) may be more visually appealing, engaging, intuitive, and attention grabbing for the user. The TIPI as shown in FIG. 9 is more reliant upon text, which can be tedious and less compelling than the visual representations of the hourglass shapes. Further, the TIPI ten-item questionnaire may be limited to seven answer options that are discrete in nature. For example, in each of the TIPI questions, the user is asked to rank himself/herself according to, e.g., seven, discrete levels—disagree strong, disagree moderately, disagree a little, neither agree/disagree, agree a little, agree moderately, and agree strongly. In contrast, each graphical psychometric test (e.g., graphical psychometric test 300) may allow a user to click on a continuous scale, thereby providing the user a much finer level of granularity of choices to choose from.

In some implementations, defining 200 the psychometric data for a user may include instructing or prompting a user (e.g., on the user interface of client electronic device 42) to "Rate yourself on the scales below. Slide the bar on the hourglass to identify where you land between each set of traits." In some implementations, interactive virtual assistant process 10 may use one or more graphical psychometric tests to define 200 the psychometric data for a user. For example and as shown in FIG. 3, interactive virtual assistant process 10 may provide e.g., five graphical psychometric tests (e.g., graphical psychometric test 300) in a sequential order. That is, a user may sequentially interact with each graphical psychometric test individually. However, it will be appreciated that more or fewer graphical psychometric tests may be utilized.

In some implementations, the one or more interactive graphical psychometric tests include one or more slidable user interface features configured to move along a continuous scale between two end points representative of a first level of a psychometric trait and a second level of the psychometric trait. For example, graphical psychometric test (e.g., graphical psychometric test 300) may include a slidable user interface feature (e.g., bar 302) configured to move along a continuous scale of response levels (e.g., response level 304) with pixel size granularity. For example, a selection near the top of an individual graphical psychometric test may denote a first level of a psychometric trait 306 (e.g., a high level of the corresponding Big Five Personality Inventory trait, conscientiousness, neuroticism, agreeableness, extraversion, or openness) and a selection near the bottom may represent a second level of the psychometric trait 308 (e.g., a low level of a given trait). In some implementations, responses near the center may suggests that the user's personality lies somewhere between the extremes of the personality dimension. In some implementations, the graphical psychometric test (e.g., graphical psychometric test 300) may be an hourglass shape that is wider at the top base and at the bottom base, but narrower in the middle. This characteristic may help a user to visualize the middle of the object, which may represents a neutral trait. One of the advantages of this shape is that it gives the user a better sense perceptually of how far or how close he is associating himself with a particular trait. Graphical psychometric test (e.g., graphical psychometric test 300) may also be symmetric along the x-axis and the y-axis. These characteristics visually invite the user to click along a centered vertical line that divides the hourglass shape equally. One of the advantages of the graphical psychometric test being shaped like an hourglass as shown in FIG. 3 is that it encourages more consistent user behavior when the user is interacting with the graphical objects.

In some embodiments and as discussed above, defining 200 psychometric data of the user may include providing one or more interactive graphical psychometric tests in a user interface of the computing device. In some implementations, five graphical interactive psychometric tests may be provided 206 to the user. In some implementations, a first interactive graphical psychometric test may relate to the Big Five dimension of conscientiousness. In the example, at the top of the interactive graphical psychometric test 300 may be the words "Tidy" and "Prepared" representative a first level of conscientiousness 306 while at the bottom of the interactive graphical psychometric test 300, the words "Disorganized" and "Carefree" appear representative a second level of conscientiousness 308. If a user clicks toward the top of the interactive graphical psychometric test in this case, they are reporting to be characterized by a high level of conscientiousness, whereas the bottom of the interactive graphical psychometric test 300 would denote low levels of conscientiousness.

In some implementations, a second interactive graphical psychometric test may relate to neuroticism. A selection near the top of the interactive graphical psychometric test, closer to the words "Anxious" and "Dramatic" may represent a high level of neuroticism, or low emotional stability. A selection near the bottom of the interactive graphical psychometric test, near the words "Relaxed" and "Calm" may denote a low level of neuroticism, or high emotional stability.

In some implementations, a third interactive graphical psychometric test may relate to the Big Five dimension of agreeableness, with the words "Cooperative" and "Accepting" at the top of the interactive graphical psychometric test and "Questioning" and "Deliberate" at the bottom. A selection near the top of the interactive graphical psychometric test may represent a high level of agreeableness, while a selection near the bottom may represent a low level of agreeableness.

In some implementations, a fourth interactive graphical psychometric test may represent the extraversion trait of the Big Five Personality Inventory. The top of the interactive graphical psychometric test may contains the words "Engaging" and "Energetic" while the bottom may state "Thoughtful" and "Reserved." A selection closer to the top of the interactive graphical psychometric test may represent a high level of extraversion, whereas a selection toward the bottom may indicate low levels of extraversion, or high levels of introversion.

In some implementations, the fifth interactive graphical psychometric test may assess levels of openness to experience. Selections at the top of the interactive graphical psychometric test, closer to the words "Creative" and "Ingenious" may indicate a high level of openness, whereas selections near the bottom of the interactive graphical psychometric test near the words "Conventional" and "Concrete" may represent low levels of openness.

In some implementations, interactive virtual assistant process 10 may include assigning 208 a user to one or more personality outcomes based upon, at least in part, the one or more interactive graphical psychometric tests provided in the user interface of the computing device. For example, when a user completes at least a portion of the one or more interactive graphical psychometric tests, the psychometric data for the user may be defined and can therefore be conducted within a short period of time. In some implementations, the responses to at least a portion (e.g., one or more of) the one or more interactive graphical psychometric tests may be used to assign 208 the user to, e.g., one of ten, possible personality outcomes. Each of the ten personality outcomes may be defined primarily by the personality trait in which the user reports to differ most from the rest of the member population. Therefore, it is the personality trait by which the user reports being the most distinctive and unique. While ten personality outcomes have been described, it will be appreciated that any number of personality incomes are within the scope of the present disclosure.

For example, psychometric data defined 200 primarily by high levels of conscientiousness may be assigned 208 by interactive virtual assistant process 10 to a personality outcome referred to as the "Architect," while users with low levels of conscientiousness may be assigned 208 by interactive virtual assistant process 10 to the "Free Spirit" personality group. If the user's most unique trait is high levels of emotional stability, then that user may be assigned 208 by interactive virtual assistant process 10 to the "Rock" personality, while low levels of emotional stability define the "Spark." In some implementations, a user reporting his/her most distinctive trait to be high levels of agreeableness may be assigned 208 by interactive virtual assistant process 10 to the "Ambassador" personality outcome and low levels of agreeableness may result in an assignment 208 of the user by interactive virtual assistant process 10 to the "Contrarian" personality outcome. Highly extroverted users may be assigned 208 by interactive virtual assistant process 10 to the "Storyteller" group, while distinctive introverts may be assigned 208 by interactive virtual assistant process 10 to the "Oasis" personality group. Finally, those most defined by high levels of openness to experience may be assigned 208 by interactive virtual assistant process 10 to the "Adventurer" personality, and those with low openness to experience may be assigned 208 to the "Guardian" personality group.

As will be discussed in greater detail below, the assignment 208 of the user by interactive virtual assistant process 10 may provide valuable insights into the financial personality of a user. For example and referring also to FIG. 4, the one or more personality outcomes may be correlated or mapped to financial characteristics associated with the user. In some implementations, by defining the one or more personality outcomes for a user, interactive virtual assistant process 10 may prompt the user, via the interactive virtual assistant, with one or more options to help the user avoid financial difficulties. In this manner and as will be discussed in greater detail below, the personalized nature of the interactive virtual assistant may be configured to help a user address financial or other difficulties that may result due to the psychometric traits of the user.

In some embodiments, a personality outcome assignment may be determined as shown below:

If MaxScale=HighConscientiousScale then return "Architect"
If MaxScale=LowConscientiousScale then return "Free Spirit"
If MaxScale=HighOpenScale then return "Adventurer"
If MaxScale=LowOpenScale then return "Guardian"
If MaxScale=HighNeuroticScale then return "Spark"
If MaxScale=LowNeuroticScale then return "Rock"
If MaxScale=HighExtraversionScale then return "Storyteller"
If MaxScale=LowExtraversionScale then return "Oasis"
If MaxScale=HighAgreeableScale then return "Ambassador"
If MaxScale=LowAgreeableScale then return "Contrarian"
Where:

MaxScale=maximum value from array {HighConscientiousScale, LowConscientiousScale, HighOpenScale, LowOpenScale, HighNeuroticScale, LowNeurotic Scale, HighExtraversionScale, LowExtraversionScale, HighAgreeableScale, LowAgreeableScale}

HighConscientiousScale=maximum between (HourglassC−ConMed) or 0
LowConscientiousScale=maximum between (ConMed−HourglassC) or 0
HighOpenScale=maximum between (HourglassO−OpenMed) or 0
LowOpenScale=maximum between (OpenMed−HourglassO) or 0
HighNeuroticScale=maximum between (HourglassN−NeurMed) or 0
LowNeuroticScale=maximum between (NeurMed−HourglassN) or 0
HighExtraversionScale=maximum between (HourglassE−ExtraMed) or 0
LowExtraversionScale=maximum between (ExtraMed−HourglassE) or 0
HighAgreeableScale=maximum between (HourglassA−AgreeMed) or 0
LowAgreeableScale=maximum between (AgreeMed−HourglassA) or 0
HourGlassO=score corresponding to an interactive graphical psychometric test related to openness
HourGlasssC=score corresponding to an interactive graphical psychometric test related to conscientiousness
HourGlassE=score corresponding to an interactive graphical psychometric test related to extraversion
HourGlassA=score corresponding to an interactive graphical psychometric test related to agreeableness
HourGlassN=score corresponding to an interactive graphical psychometric test related to neuroticism
OpenMed=population median score corresponding to an interactive graphical psychometric test related to openness ConMed=population median score corresponding to an interactive graphical psychometric test related to conscientiousness ExtraMed=population median score corresponding to an interactive graphical psychometric test related to extraversion AgreeMed=population median score corresponding to an interactive graphical psychometric test related to agreeableness NeurMed=population median score corresponding to an interactive graphical psychometric test related neuroticism In some implementations, interactive virtual assistant process 10 may provide 202 an interactive virtual assistant, selected from a plurality of interactive virtual assistants, on the computing device based upon, at least in part, the psychometric data defined for the user. An interactive virtual assistant may generally include a software agent that can perform tasks or services for an individual. In some implementations, interactive virtual assistant may interact with a user via text, voice, and/or through images or video. In some implementations and as will be discussed in greater detail below, the interactive virtual assistant may ask questions to better understand the individual user and/or the user may ask questions of the interactive virtual assistant to which interactive virtual assistant may prompt 206 the user with one or more options. As the interactive virtual assistant helps the user, the user is also providing information that will make his/her interactive virtual assistant more personalized. For example, the interactive virtual assistant may learn over time, based on personality, how the user spends his/her money, what makes the user happy, when the user feels stressed, what the user's goals are, and more. In some implementations and as will be discussed in greater detail below, interactive virtual assistant process 10 may provide an interactive virtual assistant that is able to combine the user's psychological traits, bank and credit card account transactions, credit history, and life stage information to understand the user's complete financial picture and provide personalized options and/or suggestions for the user's benefit.

In some implementations, providing the interactiveual assistant may include selecting 210 the interactive virtual assistant, from the plurality of interactive virtual assistants, for the user based upon, at least in part, the psychometric data defined 200 for the user. As discussed above and in some implementations, various interactive virtual assistants may be provided by interactive virtual assistant process 10. However, users may not always respond favorably or at all to a generic or arbitrary interactive virtual assistant. For example, a user's personality or psychometric data may heavily influence how likely the user is to respond favorably to an option or suggestion. The Applicant has observed that users are especially emotionally sensitive or unsure when making financial decisions or responding to financial options. As such, interactive virtual assistant process 10 may provide 202 an interactive virtual assistant, selected 210 from a plurality of interactive virtual assistants, on the computing device based upon the psychometric data defined 200 for the user. In some implementations, interactive virtual assistants may be initially selected 210 based on responses to the above noted psychometric tests (e.g., interactive graphical psychometric tests) related to one or more of the Big Five personality traits. In some implementations, the interactive virtual assistant may be selected 210 for the user based upon, at least in part, the user's psychometric data defined 200 for the Big Five personality traits of conscientiousness, neuroticism, and extraversion. For example and as observed by the Applicant, a k-means cluster analysis was utilized to uncover patterns of response among these three personality traits among all users who completed the one or more interactive graphical psychometric tests described above. A pattern emerged and was validated with employment of a k-fold cross-validation. Conscientiousness, neuroticism, and extraversion were the personality traits that led to the most stable and evenly spread clusters of user personalities. As will be discussed in greater detail below, these three psychometric traits (e.g., conscientiousness, neuroticism, and extraversion) may represent the traits that are most characteristic of positive or negative financial outcomes and social interaction style, providing a satisfactory basis for personalization opportunities for the interactive virtual assistants.

Figure 5:
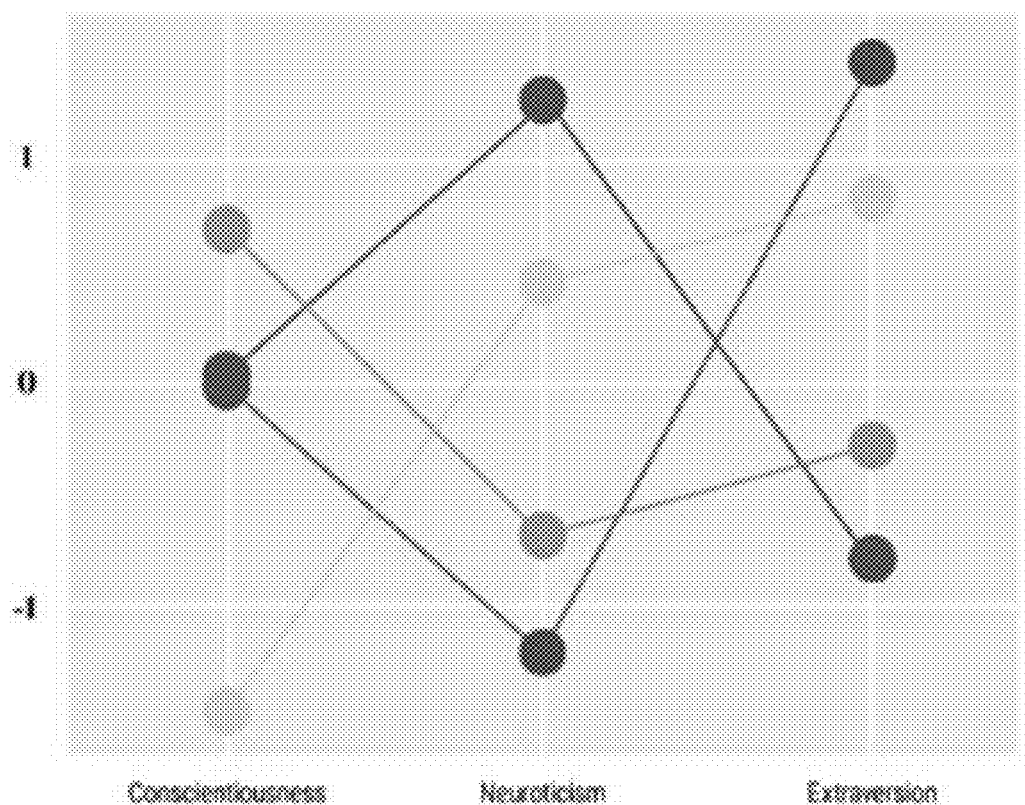
FIG. 5 is an example diagrammatic view of one or more cluster groups of users according to one or more example implementations of the disclosure.

Referring also to FIG. 5 and in some implementations, it has been observed by the Applicant that four clusters of personality traits along the three dimensions of conscientiousness, neuroticism, and extraversion, may be the most stable across user segments. In some implementations, an interactive virtual assistant may be assigned based upon, at least in part, a distance from cluster medians along said personality dimensions. For example, while personality outcomes may be assigned 208 based upon, at least in part, the most distinct personality trait response, the interactive virtual assistant process 10 may select 210 or otherwise assign a interactive virtual assistant from a plurality of interactive virtual assistants based upon, at least in part, the specific constellation of responses along the three noted personality dimensions of conscientiousness, neuroticism, and extraversion.

In some implementations and referring also to the example of FIG. 5, INTERACTIVE VIRTUAL ASSISTANT PROCESS 10 may select 210 an interactive virtual assistant for the user from the plurality of interactive virtual assistants based upon, at least in part, personality dimensions of conscientiousness, neuroticism, and extraversion defined for the user. In some implementations, interactive virtual assistant process 10 may include and/or use a first machine learning algorithm described as a four-level extreme gradient boosting classifier with a softmax learning parameter to perform multi-class classifications. In some implementations, the extreme gradient boosting classifier with a softmax learning parameter may be trained on a subset of the full user pool of users who have completed the one or more interactive graphical psychometric tests and may be tested on a set of users who were held out of training of the model. In this manner, an interactive virtual assistant may be assigned by determination of the maximum probability of cluster assignment related to the personality traits of conscientiousness, neuroticism, and extraversion, which may represent the inputs to the model.

In some implementations, interactive virtual assistant process 10 may select 210 the interactive virtual assistant from the plurality of interactive virtual assistants by a second machine learning algorithm where retraining of the machine learning model described above is deemed necessary. In this case, cluster assignment may be based upon, at least in part, a determination of the minimum absolute value distance from the medians of the personality traits associated with each cluster. For example, if the minimum absolute value distance is determined to be the distance from a first interactive virtual assistant median along conscientiousness, neuroticism, and extraversion scales, then the first interactive virtual assistant may be selected and provided to the user.

A more detailed description of the above is provided below:

If MinDistance=InteractiveVirtualAssistant1Distance then return "InteractiveVirtualAssistant 1"
If MinDistance=InteractiveVirtualAssistant2Distance then return "InteractiveVirtualAssistant 2"
If MinDistance=InteractiveVirtualAssistant3Distance then return "InteractiveVirtualAssistant 3"
If MinDistance=InteractiveVirtualAssistant4Distance then return "InteractiveVirtualAssistant 4"
where MinDistance=Select minimum value from array {InteractiveVirtualAssistant1Distance, InteractiveVirtualAssistant2Distance, InteractiveVirtualAssistant3Distance, InteractiveVirtualAssistant4Distance}

InteractiveVirtualAssistant1Distance=|Hourglass$C$−InteractiveVirtualAssistant1ConMed|+|Hourglass$N$−InteractiveVirtualAssistant1NeurMed|+1Hourglass$E$−InteractiveVirtualAssistant1ExtraMed|

InteractiveVirtualAssistant2Distance=|Hourglass$C$−InteractiveVirtualAssistant2ConMed|+|Hourglass$N$−InteractiveVirtualAssistant2NeurMed|+|Hourglass$E$−InteractiveVirtualAssistant2ExtraMed|

InteractiveVirtualAssistant3Distance=|Hourglass$C$−InteractiveVirtualAssistant3ConMed|+|Hourglass$N$−InteractiveVirtualAssistant3NeurMed|+|Hourglass$E$−InteractiveVirtualAssistant3ExtraMed|

InteractiveVirtualAssistant4Distance=|Hourglass$C$−InteractiveVirtualAssistant4ConMed|+|Hourglass$N$−InteractiveVirtualAssistant4NeurMed|+|Hourglass$E$−InteractiveVirtualAssistant4ExtraMed|

|$n$|=the absolute value of $n$

HourGlasssC=score corresponding to an interactive graphical psychometric test related to conscientiousness HourGlassE=score corresponding to an interactive graphical psychometric test related to extraversion HourGlassN=score corresponding to an interactive graphical psychometric test related to neuroticism InteractiveVirtualAssistant1ConMed=population median score corresponding to an interactive graphical psychometric test related conscientiousness for those assigned to cluster 1

InteractiveVirtualAssistant2ConMed=population median score corresponding to an interactive graphical psychometric test related conscientiousness for those assigned to cluster 2

InteractiveVirtualAssistant3 ConMed=population median score corresponding to an interactive graphical psychometric test related conscientiousness for those assigned to cluster 3

InteractiveVirtualAssistant4ConMed=population median score corresponding to an interactive graphical psychometric test related conscientiousness for those assigned to cluster 4

InteractiveVirtualAssistant1ExtraMed=population median score corresponding to an interactive graphical psychometric test related extraversion for those assigned to cluster 1

InteractiveVirtualAssistant2ExtraMed=population median score corresponding to an interactive graphical psychometric test related extraversion for those assigned to cluster 2

InteractiveVirtualAssistant3ExtraMed=population median score corresponding to an interactive graphical psychometric test related extraversion for those assigned to cluster 3

InteractiveVirtualAssistant4ExtraMed=population median score corresponding to an interactive graphical psychometric test related extraversion for those assigned to cluster 4

InteractiveVirtualAssistant1NeurMed=population median score corresponding to an interactive graphical psychometric test related neuroticism for those assigned to cluster 1

InteractiveVirtualAssistant2NeurMed=population median score corresponding to an interactive graphical psychometric test related neuroticism for those assigned to cluster 2

InteractiveVirtualAssistant3NeurMed=population median score corresponding to an interactive graphical psychometric test related neuroticism for those assigned to cluster 3

InteractiveVirtualAssistant4NeurMed=population median score corresponding to an interactive graphical psychometric test related neuroticism for those assigned to cluster 4

Figure 6:
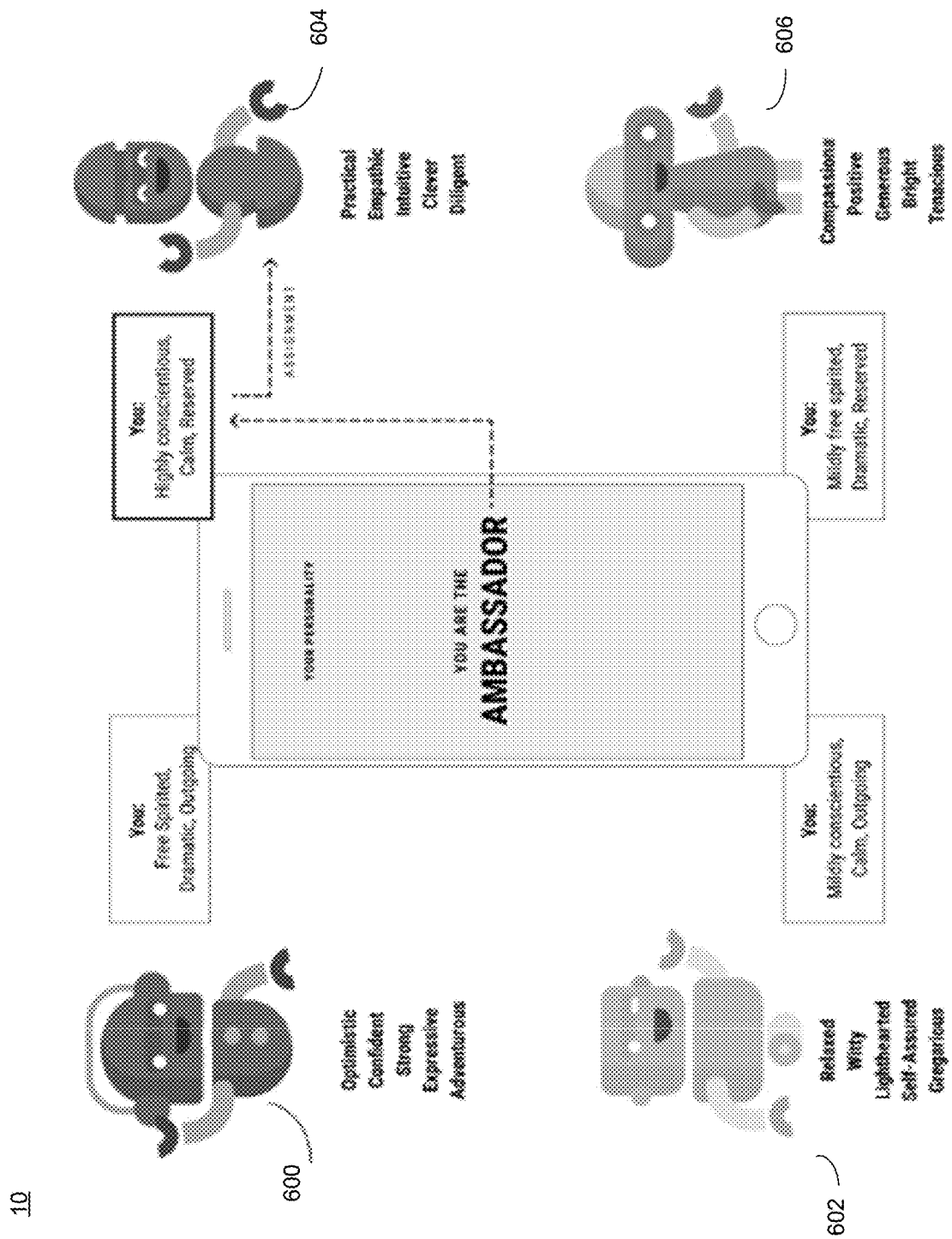
FIG. 6 is an example diagrammatic view of various interactive virtual assistants that may be provided by an interactive virtual assistant process to a user according to one or more example implementations of the disclosure.
Figure 7:
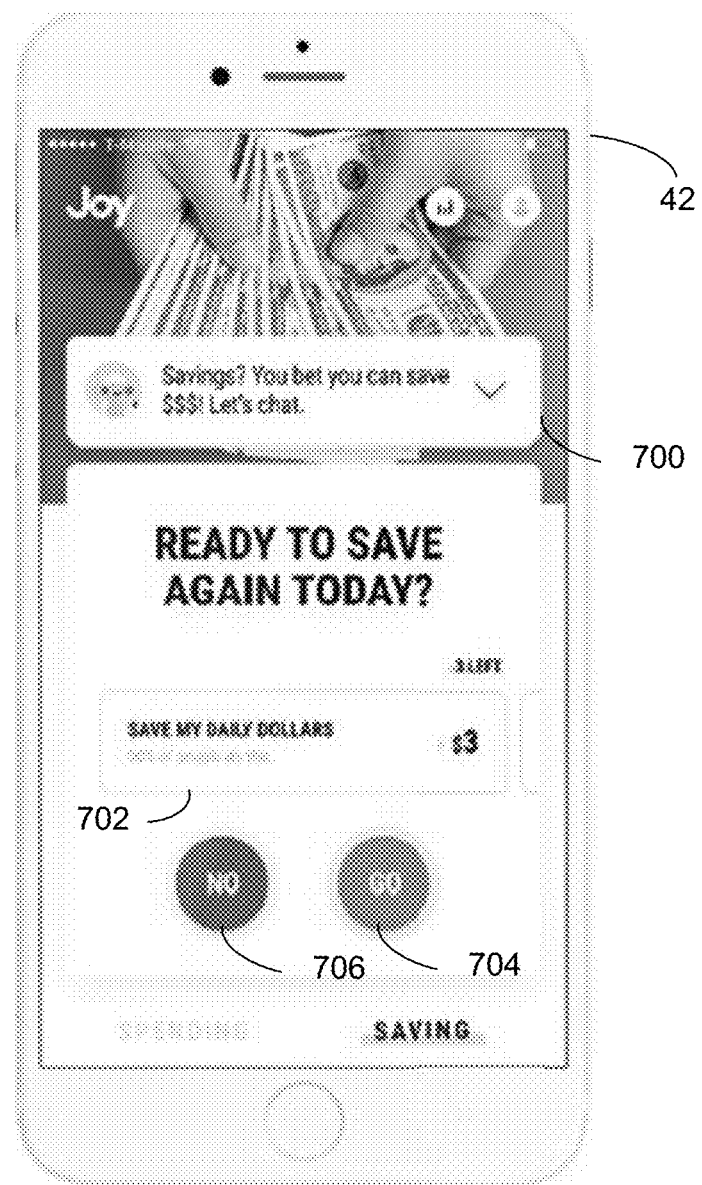
FIG. 7 is an example diagrammatic view of example prompt including one or more financial savings options provided by an interactive virtual assistant process according to one or more example implementations of the disclosure.

Referring also to FIG. 6 and in some implementations, a first interactive virtual assistant of the plurality of interactive virtual assistants; e.g., interactive virtual assistant 600, may be provided 202 to users reporting low levels of conscientiousness, high levels of neuroticism, and high levels of extraversion. To best fit the personalities of this group of users and provide welcome interactions, this interactive virtual assistant 600 may be given a personality that is described as encouraging, warm, strong, and stable. Interactive virtual assistant 600 may be nonjudgmental, may set direct expectations, and/or may maintain a fun attitude with the user.

Interactive virtual assistant 602 may be provided 202 to users reporting neutral levels of conscientiousness, low levels of neuroticism, and high levels of extraversion. To most effectively interact with this group of users, interactive virtual assistant 602 may be given characteristics of being witty, motivational, informative, skeptical, and/or non-manipulative. This interactive virtual assistant 602 may have a relaxed attitude for a relaxed set of users.

In some embodiments, interactive virtual assistant 604 may be provided 202 to users reporting neutral levels of conscientiousness, high levels of neuroticism, and low levels of extraversion. This is a reserved yet anxious set of users, which is why interactive virtual assistant 604 may be given a personality that is calm, peaceful, accepting, and nonjudgmental. This interactive virtual assistant 604 may not be pushy with advice, may focuses more on positive feedback than pointing out areas in need of improvement, and/or may approach the user with patience and understanding.

Interactive virtual assistant 606 is assigned to users reporting high levels of conscientiousness, mid to low levels of neuroticism, and mid to low levels of extraversion. Users who are provided 202 interactive virtual assistant 606 by interactive virtual assistant process 10 may be well informed and appreciate a traditional style of financial advisor, which is why interactive virtual assistant 606 may be informative, clear, and dependable, while occasionally being fun and surprising. Interactive virtual assistant 606 may get straight to the facts without "sugar coating" information and may focus more on areas in need of improvement than on praise. While four interactive virtual assistants have been described, it will be appreciated that any number of interactive virtual assistants are possible within the scope of the present disclosure.

In some implementations, interactive virtual assistant process 10 may prompt 204 the user, via the interactive virtual assistant, with one or more options. For example, interactive virtual assistants provided 202 by interactive virtual assistant process 10 may be configured with the ability to react to user behavior based upon, at least in part, a dynamic conversational algorithm in order to prompt 204 the user or otherwise provide the user with personalized options. For example, any conversation that the user is engaged in may be compared to the previous engagement in the same conversation. Base levels and delta scores may be calculated for any quantitative behavioral or financial value that is discussed in the conversation. Base levels and delta scores may dictate the tenor of the interactive virtual assistant response. The base level may generally refer to where the user's score falls within the full range of possible scores. The delta may be calculated by the change in base level from the previous conversation to the present conversation. Positive delta scores may result in a congratulatory response from the interactive virtual assistant, negative scores may result in a supportive challenge from the interactive virtual assistant, and scores of zero (or no change), may result in a neutral response from the interactive virtual assistant. The current base level may also be accounted for in the response of the interactive virtual assistant, as a small negative delta from an already high base level score is likely a bit less negative for a user than a slight increase in delta on a very low base level score. Thus base level responses and delta responses may be two contributing components to interactive virtual assistant responses.

In some implementations, responses of an interactive virtual assistant may be organized into no fewer than e.g., five levels for delta scores, including, large improvement, small improvement, no change, small set-back, and large set-back. While five delta score levels have been described, it will be appreciated that any number of levels of delta scores is possible and within the scope of the present disclosure. Similarly, base level responses may be organized into e.g., five levels, very high, high, mid, low, and very low. In some implementations, the organization of base level responses may be referred to as buckets. Buckets may be assigned based on quantile levels of either the user's historic data or segment population data, whichever is relevant in the given conversation. Interactive virtual assistant responses may be automated, where the response level selected may be determined by the corresponding delta and base level score calculations.

In order to ensure that conversations do not become repetitive, interactive virtual assistant process 10 may include an input-tagging system. Input tagging may occur when words or phrases in a sentence are made replaceable by a bin of selected words or phrases that can be used in their place. For example, the word "Hello" can be replaced by a selection from an array of options including, "Hi", "Howdy", "Hey there", "How's it going", or "What's up". Below is an example paragraph using the input-tagging system of interactive virtual assistant process 10.

(Overall Reaction) (#1 Happy Spend) (#2 Happy Spend) (#3 Happy Spend) (#4 Happy Spend) (#5 Happy Spend).

Results Paragraph—Variables $size_large $movement_noun in the Top 5 Happy Spends $time_week, $name. $number_one_reaction. $number_one_ company at #1 $again with $number_one_happy_spends happy spends $time_week_blanks. $fun_fact. $number_two_last_week_movement, $number_two_company is the #2 happy spend $time_week_blanks with $number_two_happy_spends. Then $number_three_company $number_two_last_week_movement to #3 with $number_three_happy_spends. And with $number_four_happy_spends, $number_four_fun_fact, $number_four_company $arrives at #4. $number_five_intro, $number_five_ company with $number_five_happy_spends, $number_five_fun_fact.

Results Paragraph—Single Written Example

"A lot of movement in the Top 5 happy spends this week, Clara. No change at the top, though. Starbucks is #1 again with 4,576 happy spends. This is their 5th week in a row on top. Three more weeks and they will break Target's 8-week record from summer 2011. Up two spots from #4 last week, Target is the #2 this week with 3,879 happy spends. Then Amazon falls one spot from last week to #3 with 2,876. And with 2,111 happy spends, an all-time high, iTunes comes in at #4. Rounding out the top 5, is Costco with 1,743."

As can be seen from at least the above example paragraphs and in some implementations, interactive virtual assistant process 10 may provide 202 an interactive virtual assistant configured to prompt 204 the user with one or more personalized options based upon, at least in part, feedback from the user. In this way, interactive virtual assistant process 10 may generate one or more prompts based upon, at least in part, configurable prompt variables. In some implementations, these configurable prompt variables may be based upon, at least in part, psychometric data defined 200 for a user. For example, based on the personality outcomes assigned 208 to the user, interactive virtual assistant process 10 may adjust the configurable prompt variables to include one or more phrases or expressions that are specific to each personality outcome.

For example, an interactive virtual assistant may be configured to provide advice to a particularly sensitive user differently than a less sensitive user. Additionally, an interactive virtual assistant may respond to a user using "emojis" or other ideograms when the user's personality has been defined to respond favorably to more friendly and more fun interactions. In some implementations, interactive virtual assistant process 10 may generate dynamic prompts for the interactive virtual assistants that are customized to a user based on historical feedback from the user and/or defined for various personality types. In some implementations, certain interactive virtual assistants may be configured to provide more prompts than other interactive virtual assistants. For example, a first interactive virtual assistant may be configured to respond well to users who are more serious. In this example, interactive virtual assistant process 10 may provide the first interactive virtual assistant with shorter, more specific prompts. In another example, a second interactive virtual assistant may be configured to respond well to users who are more free-spirited or less serious. In this example, interactive virtual assistant process 10 may provide the second interactive virtual assistant with longer, more conversational prompts. It will be appreciated that interactive virtual assistant process 10 may configure the interactive virtual assistants in various ways based upon, at least in part, the psychometric data defined 200 for a user.

In some implementations, interactive virtual assistant process 10 may configure the prompts of the interactive virtual assistant based upon, at least in part, one or more machine learning algorithms. For example, with more experience from users interacting with various interactive virtual assistants, interactive virtual assistant process 10 may provide this data to one or more machine learning algorithms to predict which prompts, phrases, frequencies of contact, etc. will be best received by various users with various psychometric traits. In this way, interactive virtual assistant process 10 may provide an interactive virtual assistant that dynamically responds to a user individually and to users generally based on their psychometric traits.

In some implementations and as discussed above, the interactive virtual assistant may be configured to prompt the user with the one or more financial options via an interactive electronic communication session displayed in a user interface of the computing device. In some implementations, interactive virtual assistant process 10 may receive one or more questions, comments, or other input from a user in an interactive electronic communication session displayed in a user interface. For example, a user of a mobile device (e.g., client electronic device 42) may initiate an interactive electronic communication session via interactive virtual assistant process 10. In some implementations, interactive virtual assistant process 10 may provide 202 an interactive virtual assistant to user (as discussed above). In some implementations, the user may request information (e.g., by providing a question in the interactive electronic communication session) from the interactive virtual assistant. In some implementations and as will be discussed in greater detail below, the interactive virtual assistant may prompt 206 the user with one or more options based upon, at least in part, the defined psychometric data.

In some implementations, prompting 204 the user, via the interactive virtual assistant, with one or more options may include prompting 212 the user with one or more financial savings options. For example, embodiments of interactive virtual assistant process 10 may assist users in developing a habit around saving money to reduce levels of stress and increase feelings of security. In some implementations and referring also to FIG. 7, interactive virtual assistant process 10 may prompt 212 a user with one or more financial savings options (e.g., financial savings option 700) via the interactive virtual assistant (e.g., interactive virtual assistant 702). In some implementations, interactive virtual assistant process 10, via the interactive virtual assistant, may prompt the user with a daily savings amount and in response to which, the user may opt-in to savings by clicking the opt-in option (e.g., or opt-out by selecting the option to denote opting-out. The user is put in control of opting-in or out of the savings suggestion each day in order to enhance engagement with finances and to promote habit formation around saving money. Embodiments of the present disclosure may allow a user to have the sense that taking action is allowing for greater control over financial outcomes. For example, a user may select a "Go" feature button 704) to opt-in to the financial savings option or a user may select a "No" feature (e.g., button 706) to opt-out of the financial savings option. While two buttons have been presented, it will be appreciated that other modalities for opting in or out of the financial savings options are possible such a voice command from the user or a text-based response in an electronic communication session with the interactive virtual assistant.

In some implementations, interactive virtual assistant process 10 may generate the one or more financial savings options by prompting the user for certain financial information. For example, interactive virtual assistant process 10 may prompt a user to report their net annual income or income after paying taxes for the year. Interactive virtual assistant process 10 may prompt users to report how much money is spent on housing payments each month. In order to view purchase transactions, interactive virtual assistant process 10 may request user permission to link to all active bank accounts and credit card accounts, providing all relevant transaction data necessary for the calculation of available discretionary income and the total amount spent on recurring payments or bills each month.

In some implementations, interactive virtual assistant process 10 may calculate the sum of recurring payments for the last e.g., thirty days. To achieve this, the user's full transaction stream is considered. The transaction description related to the recurring payment may have occurred at a minimum of e.g., three times in the transaction history. A transaction is defined as a recurring payment if it reaches a criteria of having a frequency stability score of less than the threshold value of e.g., 0.25, a stable score in this case is closer to zero while larger scores are more unstable across time. The frequency stability score may be calculated by interactive virtual assistant process 10 using an interquartile range mean ratio, meaning that the average time, in days, between the purchases occurring at frequencies within the e.g., 20th and e.g., 80th percentile frequencies is divided by the number of days since the last purchase or payment matching the transaction description. The thirty day window may ensure a moving average that is most current for each recurring payment made.

In some implementations, a user's current available discretionary income amount may be calculated by interactive virtual assistant process 10 by subtracting reported housing pay, the sum of all recurring payments for the past e.g., thirty days divided by the number days in the payment period and the user's current cumulative payment period spend amount from the user's calculated income if available, and reported income if not available. The cumulative payment period spend amount may be calculated by interactive virtual assistant process 10 by the sum of all transactions in the current pay period after filtering any transaction flagged as a recurring payment, a house payment, a transfer, or a credit to the user's account.

Following the calculation of current available discretionary income, interactive virtual assistant process 10 may divide that total by the number of days remaining in the user's pay period and multiplied by a small percentage to calculate the daily safe-to-save dollar amount. The percentage multiplier is used to ensure that money is still available following opting-in to the daily savings option. Initially, the percentage is set to e.g., 3% of available discretionary income divided by the current week in the month, but is open to the user's adjustment following an initial exposure period. In some implementations, a user may adjust the percentage via a user interface. Percentages may increase for those who want to be more aggressive in their savings, and may decrease for those wishing to be more conservative. Taking the percentage from the calculated available discretionary income may ensure that users will not save more than they have available.

With use of the above described process for calculating a daily safe-to-save dollar amount, the suggested amount as determined by interactive virtual assistant process 10 may vary from day to day based on the amount of spending the user engaged in during the previous day. High levels of spending may result in a lower financial savings option, while low levels of spending may increase the financial savings option.

In some implementations, the user may be protected from saving money that is unavailable, as any calculation resulting in an output of zero or a negative amount will represent a value denoting insufficient funds to meet current expenses and thus no savings amount will be provided via the interactive virtual assistant. To address potential user errors or errors in the execution of interactive virtual assistant process 10, a user who receives a $0 savings suggestion will be prompted 204 by the interactive virtual assistant to check their reported income and housing payment, and to verify that all bank and credit card accounts are properly linked to ensure accurate calculations.

Figure 8:
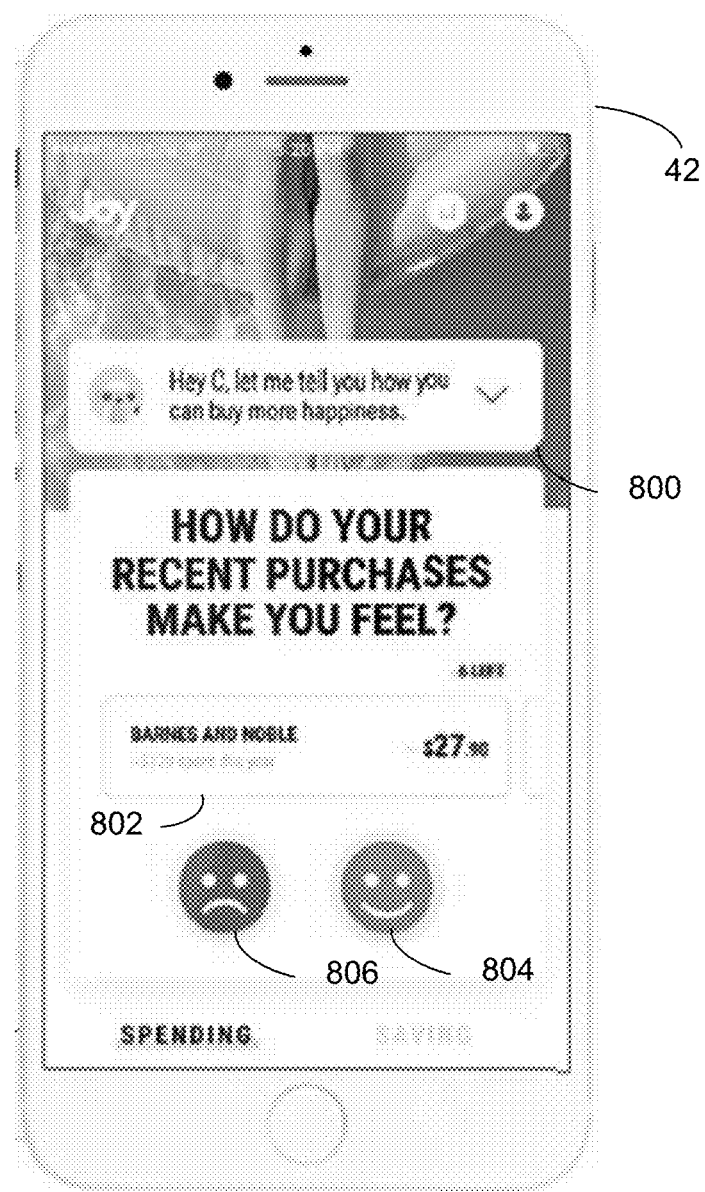
FIG. 8 is an example diagrammatic view of an example prompt including a prompt to rate one or more financial transactions provided by an interactive virtual assistant process according to one or more example implementations of the disclosure.

The one or more financial savings options may be calculated as shown below:

Financial Savings Option Value=(CurrentDiscretionIncome/DaysRemainingInPayPeriod)*CurrentSavingPercentage Where
CurrentDiscretionaIncome=(CalculatedMonthlyIncome/ AvgPaymentsPerMonth or StatedAnnualIncome/12)− StatedHousingPayment−RecurringBills30Days CurrentPayPeriodDiscretionarySpend
DaysRemainingInPayPeriod=The number of days remaining in current month
Current SavingPercentage=Set initially at 3% but open to adjustment after initial exposure period
CalculatedMonthlyIncome=Sum of income payments in the last 30 days AvgPaymentsPerMonth=The number of payments the user receives per month (yearly payments/12)
StatedAnnualIcome=User reported income
StateHousingPayment=User reported housing payment
RecurringBills30Days=Sum of recurring payments in the last 30 days CurrentPayPeriodMonthlyDiscretionarySpend=Sum of all transaction debit amounts after filtering recurring payments, housing payments, and transfers In some implementations and referring also to FIG. 8, prompting 204 the user, via the interactive virtual assistant, with one or more options may include prompting 214 the user to rate one or more financial transactions. For example, one or more transactions available in a user's transaction history may be provided by interactive virtual assistant process 10, via the interactive virtual assistant (e.g., interactive virtual assistant 800), for rating with an emotional spend annotation. In some implementations, a user may be prompted 214 by the interactive virtual assistant to reflect upon one or more recent transactions or purchases (e.g., prompt 802) and if the purchase was deemed satisfying (i.e., does the transaction make the user more happy), select a first emotional annotation (e.g., selection of a green smiling face button 804). If a given purchase leads to feelings of remorse or regret (i.e., does the transaction make the user more sad), a selection of a second emotional annotation may be received (e.g., selection of a red sad face button 806). In this manner, a user may, via interactive virtual assistant process 10, provide an emotional rating relative to their transactions. While two example emotional annotations have been provided, it will be appreciated that any number of emotional annotations and scales of emotional responses may be provided for user feedback. For example, a user may be prompted 214 by the interactive virtual assistant to reflect upon one or more recent transactions or purchases (e.g., prompt 802) and if the purchase was deemed to be a material transactions, select an emotional annotation associated with material purchases and/or if a given transaction was experiential, a selection of an emotional annotation associated with experiential transactions may be received. In some implementations, a user may be prompted 214 by the interactive virtual assistant to reflect upon one or more recent transactions or purchases (e.g., prompt 802) and if the transactions was made for the user, select an emotional annotation associated with transactions made for the user and/or if a given transactions was made for another individual, a selection of an emotional annotation associated with transactions for others may be received.

In some implementations, a user may be prompted 214 by the interactive virtual assistant to reflect upon one or more recent transactions or purchases (e.g., prompt 802) and if the transactions was a habitual transaction, select an emotional annotation associated with habitual transactions and/or if a given transaction was a non-habitual transaction (i.e., a "special treat"), a selection of an emotional annotation associated with non-habitual transactions may be received. In some implementations, the user may be prompted 214 to rate one or more transactions to rate the transaction as being a transaction made for current or immediate purposes (i.e., a transaction made for now and not directly related to the future) and/or to rate the transaction as being made for the future (e.g., an investment). As discussed above, interactive virtual assistant process 10 may prompt the user to rate the one or more transactions with an emotional annotation associated with transactions made for now and an emotional annotation associated with transactions made for the future. In some implementations, the user may be prompted 214 by interactive virtual assistant process 10, via the interactive virtual assistant, to rate one or more transactions as a time saving purchase or a non-time saving purchase. For example, the purchase of e.g., a robotic vacuum may be a transaction that would save time relative to using other manual vacuums. As discussed above, interactive virtual assistant process 10 may prompt the user to rate these transactions with one or more emotional annotations. While buttons have been discussed as examples of emotional annotations, it will be appreciated that other forms of user selection or input may be used within the scope of the present disclosure to emotionally annotate one or more transactions via interactive virtual assistant process 10.

In some implementations, prompting 214 the user to rate one or more financial transactions may include prompting the user to associate the one or more financial transactions with one or more categories. For example, interactive virtual assistant process 10 may prompt the user, via the interactive virtual assistant (e.g., interactive virtual assistant 800) to associate the financial transaction with one or more categories. In some implementations, the categories may be predefined categories and/or may be defined by a user when associating the financial transaction to a newly defined category. In some implementations, associating the financial transaction with a category may include tagging the financial transaction with the category. In some implementations, interactive virtual assistant process may utilize these categories to provide insights to the user regarding their spending habits.

In some implementations, emotional ratings may be used to categorize transactions into categories that are meaningful and relevant to the user on an individual level. This form of categorization has an advantage over typical spend categorization labels created by third party transaction data platforms or by in-house transaction description driven categorization algorithms in that the user himself/herself is responsible for the categorization which leads to fewer doubts of categorization accuracy or authenticity. It has the added advantage of engaging the user with purchase decisions after the purchase has been made to reflect upon said purchase and gather insight about whether a similar purchase should be made in the future.

In some implementations, the one or more rated transactions may be employed by interactive virtual assistant process 10 to drive insights delivered by interactive virtual assistant in e.g., chat dialogues or other electronic communication sessions. These insights may be made on a purely individual level, as well as aggregate levels including, but not limited to, all users of interactive virtual assistant process 10 and/or all members with the same psychometric traits (as discussed above). Insights created on the individual level and provided by the interactive virtual assistant may give the user a better understanding of how purchases make him/her feel and will allow for enhanced future assessments of the emotional response that is likely to follow a current purchase. Aggregated insights provided by the interactive virtual assistant may give the user ideas of what types of purchases are leading to happiness for other Joy members or those in a similar cohort to the user. Aggregated insights include, but are not limited to a number of top locations leading to positive or happy ratings among users (e.g., top five), a number of top locations leading to negative or sad ratings among users (e.g., top five), a number of top locations leading to positive or happy ratings among users belonging to the same personality group, and/or a number of top locations leading to negative or sad ratings among users belonging to the same personality group. In some implementations, other groupings may be used to provide aggregated insights, such as users of the same gender, user of the same or similar age (e.g., within a predefined threshold), users within a predefined distance of each other, etc. It will be appreciated various groups of users may be used to compare users. It will also be appreciated that various insights may be provided to the user based upon, at least in part, the emotional annotations provided by the user to rate the one or more transactions.

In some implementations, rankings can be given across any time period including, but not limited to, daily ratings, weekly ratings, monthly ratings, and all time ratings. Ratings will be stored for each individual user and may be reintroduced by the interactive virtual assistant following a specified time period for further reflection and reassessment of the purchase.

Figure 4:
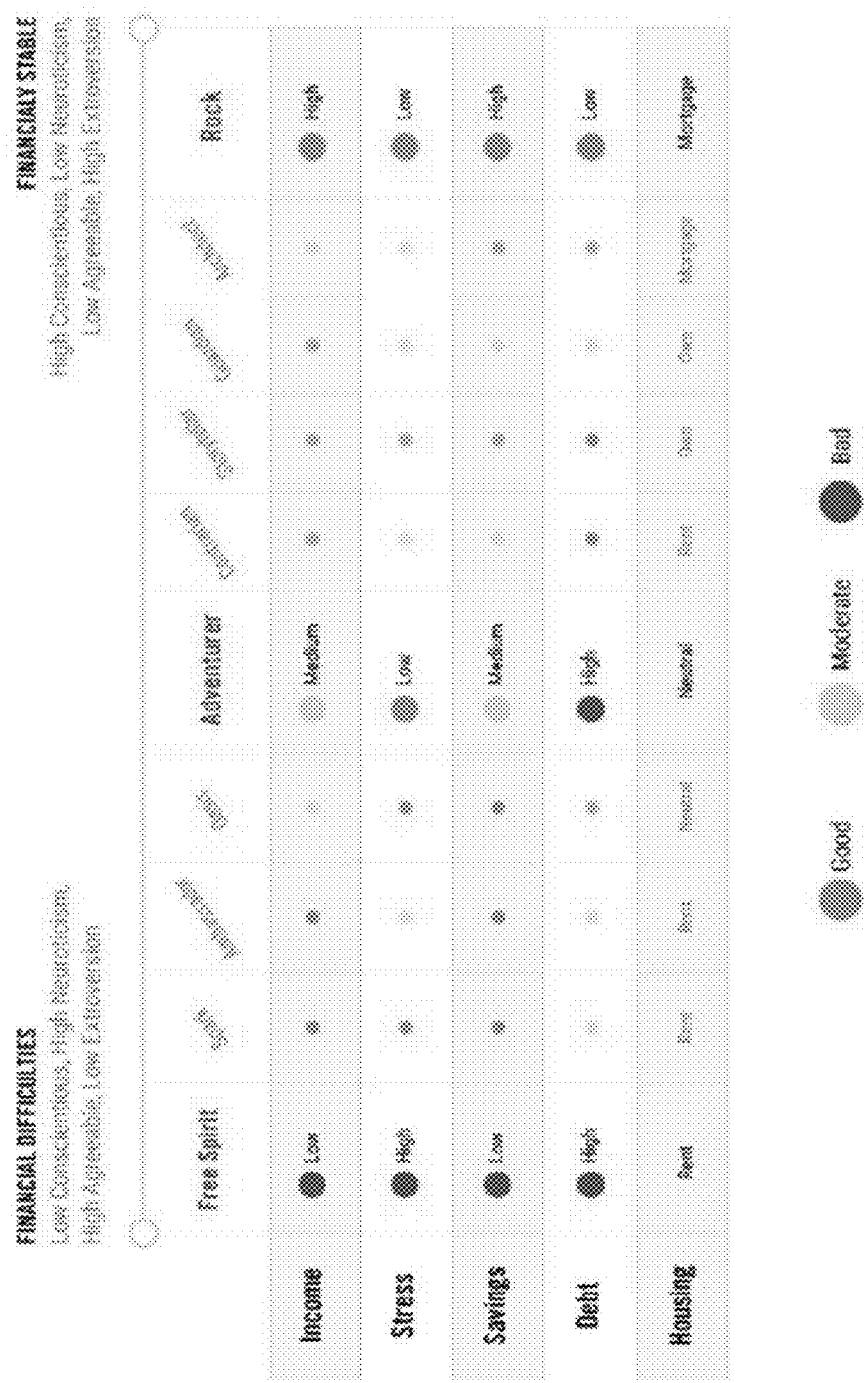
FIG. 4 is an example diagrammatic view of personality outcomes assigned for various users and associated financial characteristics for the personality outcomes according to one or more example implementations of the disclosure.

In some implementations, prompting 204 the user, via the interactive virtual assistant, with one or more options may include prompting 216 the user with one or more financial services options. For example, interactive virtual assistant process 10 may prompt the user with options for financial services such as, but not limited to, loans, insurance plans, investments, stocks, bonds, or financial instruments. For example, interactive virtual assistant process 10 may conduct one or more interactive electronic communication sessions, via the interactive virtual assistant, with the user. The user may share with the interactive virtual assistant plans or dreams of purchasing a new home. In response to this communication and based upon, at least in part, personality outcomes assigned 208 to the user, interactive virtual assistant process 10 may prompt 216 the user with one or more financial services options (i.e., a loan for a new home). For example and as shown in FIG. 4, certain personality outcomes may be more or less susceptible to financial difficulties. As such, interactive virtual assistant process 10 may filter one or more candidate financial services options from a plurality of available financial services. In some implementations, interactive virtual assistant process 10 may receive a list or otherwise communicate with a database of available financial services options. While a loan has been discussed, it will be appreciated that interactive virtual assistant process 10 may prompt 216 the user with various other financial services options.

In some implementations, prompting 204 the user, via the interactive virtual assistant, with one or more options may include prompting 218 the user with one or more recommendations to help alleviate financial stress. In some implementations, interactive virtual assistant process 10 may prompt 218 the user with one or more recommendations to help alleviate financial stress and contribute to a user's overall happiness and well-being. For example and in some implementations, interactive virtual assistant process 10 may generate an assessment of financial stress levels to determine levels of financial stress experienced by individual users to prompt 218 the user with one or more recommendations and treatment options to help alleviate experienced stress related to financial conditions. In some implementations, the assessment generated by interactive virtual assistant process 10 may generally be referred to as the Assessment of Financially Induced Stress (AFiS). For example, this assessment may be modeled after the Post Traumatic Stress Disorder (PTSD) Checklist-Civilian Version (PCL-C), which is provided in FIG. 10, as research conducted by the Applicant indicated that stress related to financial troubles resulted in a manifestation of symptoms similar to those experienced as a result of posttraumatic stress. In order to adapt the PCL-C to assess financially induced stress, items of the PCL-C may be reworded to include the word "financial" whenever experiences were discussed. In some implementations of the administration of the PCL-C, users are instructed to respond with an "X" to mark the degree to which they have "been bothered by that problem in the past month." Participants are then given five discrete response choices, including, "not at all," "a little bit," "moderately," "quite a bit," and "extremely."

The response choices provided in the AFiS by interactive virtual assistant process 10 may be identical to those provided in the PCL-C, as seen in FIG. 10. In contrast to the PCL-C which includes 17 items, the AFiS provided by interactive virtual assistant process 10 may include e.g., six items, which may be the least number of items deemed acceptable to assess the three symptom subscales of the assessment without losing statistical reliability below a commonly accepted Cronbach's alpha threshold. To reduce the items, a factor analysis may be conducted and the highest loading items among the three symptom subscales of thoughts, behaviors, and emotions, may be selected. This item reduction technique has the added advantage of reducing the assessment time for the user without losing reliability of the measure. In an embodiment of the present disclosure, a total of four nation-wide surveys conducted by a third party polling company with a sample size of over 9,000 participants was utilized to validate the measure.

It should be recognized that a greater number of items and/or different combination of PCL-C-based items (or similar items based on a non-PCL-C source) may be used in the AFiS, and variations on the scoring described below may be used, in practicing the invention described herein.

Scoring of the AFiS may, for example, also be done in a fashion similar to the scoring of the PCL-C. A sum score of the responses to each item may be added up to get a general sense of stress level experienced in the past month, or sums may be calculated within each subscale to determine individual contributions of the thoughts subscale, the emotions subscale, and the behaviors to overall stress levels. Values of responses may be scored as follows: "Not at all"=1; "A little bit"=2; "Moderately"=3; "Quite a bit"=4; "Extremely"=5.

In order to reach diagnostic criteria for a diagnosis of PTSD, a subject may endorse symptomatic levels, meaning a rating score of three or above for at least one item of the five items composing the thoughts subscale, three items from the seven items possible in the emotions subscale and at least two items of the five possible items related to the behaviors scale. Scoring of the AFiS may be kept conservative with requirements of one out of the two items of the thoughts scale, two out of the two items of the emotions scale, and two of the two items of the behaviors scale needed to reach diagnostic criteria.

Below are some examples of items of the AFiS categorized by subscale.

Thoughts Subscale Item 1=In the past month, to what degree have you felt very upset when something reminded you of a stressful financial experience from the past?

Thoughts Subscale Item 2=In the past month, to what degree have you suddenly acted or felt as if a stressful financial experience was happening again, as if you were reliving it?

Emotions Subscale Item 1=In the past month, to what degree have you felt a loss of interest in things that you used to enjoy because of your financial situation?

Emotions Subscale Item 2=In the past month, to what degree has a financial situation made you feel distant or cut off from other people?

Behaviors Subscale Item 1=In the past month, to what degree have you had difficulty concentrating because of your financial situation?

Behaviors Subscale Item 2=In the past month, to what degree have you felt irritable or had angry outbursts because of your financial situation?

The diagnostic condition has been labeled Acute Financial Stress and is considered the financially induced equivalent of PTSD. It should be made clear that this diagnosis is not included in the current Diagnostic Statistical Manual used by clinicians, but that the Applicant urges the diagnostic consideration of financially induced stress. For example, approximately 23% of Americans suffer from diagnostic levels of Acute Financial Stress according to the four nation-wide surveys conducted by the third party polling company.

In response to the assessment provided by interactive virtual assistant process 10, a user experiencing symptoms of financially induced stress may be prompted 218 by the interactive virtual assistant with the option of engaging in a series of cognitive behavioral therapy (CBT) techniques designed to help reduce stress. The techniques may include, but are not limited to: Negative Thought Replacement, Name it to Tame It, Progressive Relaxation, Telling Your Money Story, and Mindfulness Exercises.

Negative Thought Replacement may be characterized by identifying common negative thoughts related to financial issues that the user experiences, then working to replace those thoughts with more positive and productive alternatives.

When engaged in the Name It To Tame It technique, the first step may involve asking the user to give a name to his/her feelings of financial stress, which helps the user identify it as an annoying factor in his/her life and know when it is happening. The second step may involve the user tracking where and when the financial stress impacts him/her.

Progressive Relaxation is a technique employed to reduce the physical manifestations of stress. Users are trained, by the interactive virtual assistant, in various progressive relaxation techniques in order combat the unwanted stress caused by financial stress that is experienced in daily life.

When engaged in the Telling Your Money Story exercises, users are asked specific questions about their past experiences with financial issues as a way to relieve the frustrations caused by repressed feelings. Sharing the story can be therapeutic even if only shared with an interactive virtual assistant.

Mindfulness Exercises may involve observing behaviors, thoughts, and emotions rather than reacting automatically to them. The exercises are generally characterized by being aware without trying to fix or change anything. For example, users may be asked to engage in controlled breathing exercises to reduce stress. These techniques have proven helpful for many types of stress, which is why users are urged to engage in these exercises or something similar each day.

In this manner, interactive virtual assistant process 10 may prompt 218 the user with one or more recommendations to help alleviate financial stress and contribute to a user's overall happiness and well-being. For example, by providing the recommendations as described above, interactive virtual assistant process 10 may help the user to appropriately identify and respond to financial stress and as such, help increase the user's overall feeling of happiness and well-being.

The AFS diagnosis may be calculated as shown below:

$$\text{AFS\_Diagnosis=if (AFS\_Thoughts1>=3 or AFS\_Thoughts2>=3) and (AFS\_Emotions1>=3 and AFS\_Emotions2>=3) and (AFS\_Behaviors1>=3 and AFS\_Behaviors2>=3) then return "Positive" otherwise return "Negative"}$$

where
AFS_Thoughts1=Response value associated with user response to the first Thoughts subscale item.
AFS_Thoughts2=Response value associated with user response to the second Thoughts subscale item.
AFS_Emotions1=Response value associated with user response to the first Emotions subscale item.
AFS_Emotions2=Response value associated with user response to the second Emotions subscale item.
AFS_Behaviors1=Response value associated with user response to the first Behaviors subscale item.
AFS_Behaviors2=Response value associated with user response to the second Behaviors subscale item.

In some implementations, interactive virtual assistant process 10 may provide an assessment of an individual's locus of control (LOC) that may be employed by interactive virtual assistant process 10 to understand the degree to which the individual believes that he/she controls the events in his/her life. Individuals who believe that they have ultimate control over the events in their lives are said to have a high level of internal LOC. Those who believe that events in their lives are caused by influential others, luck or chance are said to have a high level of external LOC. Levels of internal and external LOC have been associated with financial outcomes such as income, credit scores, and savings balances, according to research conducted by the Applicant through the administration of a nation-wide survey through a third party national polling company. For this reason, a financially relevant LOC scale was designed and tested.

To enhance validity and reliability of the financial locus of control (FinLOC) scale, items from the Multidimensional Health Locus of Control (MHLOC) were reworded to give focus to events that are financial in nature. For example, a MHLOC item that had been worded: "I am directly responsible for my condition getting better or worse." Was then changed to: "I am directly responsible for my financial well-being."

The response choices provided in the FinLOC scale are identical to those provided in the MHLOC questionnaire. Users are given six discrete response choices, including, "Strongly Disagree," "Disagree," "Slightly Disagree," "Slightly Agree," "Agree," and "Strongly Agree." In some implementations, users may be prompted 218 simply to report the degree to which they agree or disagree with the following statements.

While the MHLOC questionnaire includes a total of 54 items on three forms, the FinLOC includes six items, which was the least number of items deemed acceptable to assess reliable measures of internal and external LOC without losing statistical reliability below a commonly accepted Cronbach's alpha threshold. To reduce the items, a factor analysis was conducted and the highest loading items among the internal and external subscale were selected. This item reduction technique has the added advantage of reducing the assessment time for the user without losing reliability of the measure. It should be noted that the MHLOC includes two subscales related to an external LOC, including the Powerful Others subscale and the Chance subscale. However, key financial outcomes were more strongly associated with the Chance subscale, so the Powerful Others subscale was dropped from the FinLOC to further reduce the length of the assessment thus reducing the strain on the user to complete the assessment.

It should be recognized that a greater number of items and/or different combination of MHLOC-based items (or similar items based on a non-MHLOC source) may be used in the FinLOC, and variations on the scoring described below may be used, in practicing the invention described herein.

In some implementations, scoring of the FinLOC may be done in a fashion similar to the scoring of the MHLOC. A sum score of the responses to internal and external questions are calculated to evaluate the strength of contribution of each scale to the user's LOC. For example, values of responses may be scored by as follows: "Strongly Disagree"=1; "Disagree"=2; "Slightly Disagree"=3; "Slightly Agree"=4; "Agree"=5; "Strongly Agree"=6.

The internal and external subscales may be scored separately and have been relabeled to reflect the "Driver" score and the "Passenger" score, respectively. The Driver and Passenger labels have been created to create a more intuitive understanding of LOC for users. Someone with a high Driver score is said to have a strong internal LOC and believes to be in control of the events shaping his/her financial life. In contrast, a user with a high Passenger score has a high external LOC and tends to believe that outside forces are controlling the events of his/her financial life.

Below are some example items of the FinLOC categorized by subscale:
Driver Subscale Item 1=I am directly responsible for my financial well-being.
Driver Subscale Item 2=Whatever goes wrong for me financially is my own fault.
Driver Subscale Item 3=My financial well-being depends on how well I take care of my spending behavior.
Passenger Subscale Item 1=It seems as though my financial health is greatly influenced by accidental occurrences.
Passenger Subscale Item 2=When I'm doing well financially, it's because I'm just plain lucky.
Passenger Subscale Item 3=No matter what I do, I'm likely to have financial problems.

The Driver and Passenger scores associated with the FinLOC may be calculated by interactive virtual assistant process 10 as follows:

$$DriverScore = DriverItem1 + DriverItem2 + DriverItem3$$

$$PassengerScore = PassengerItem1 + PassengerItem2 + PassengerItem3$$

Where:
DriverItem1=The response value associated with the user's response to the first item on the Driver subscale.
DriverItem2=The response value associated with the user's response to the second item on the Driver subscale.
DriverItem3=The response value associated with the user's response to the third item on the Driver subscale.
PassengerItem1=The response value associated with the user's response to the first item on the Passenger subscale.
PassengerItem2=The response value associated with the user's response to the second item on the Passenger subscale.
PassengerItem3=The response value associated with the user's response to the third item on the Passenger subscale.

In some implementations, prompts provided by interactive virtual assistant process 10 may be based upon, at least in part, the financial locus of control. For example, interactive virtual assistant process 10 may prompt 204 the user with one or more options specific to the user based upon, at least in part, the financial locus of control.

Figure 11:
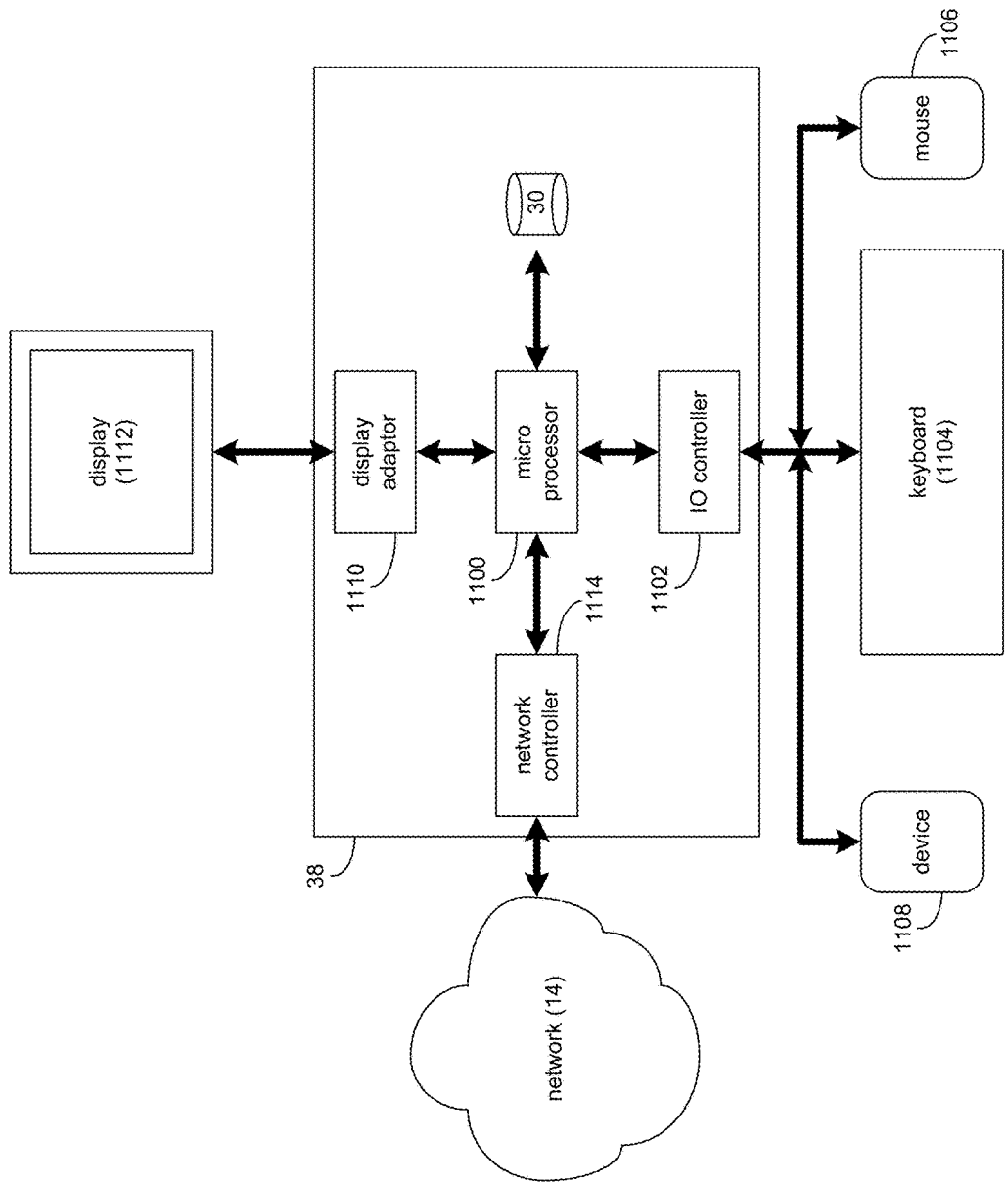
FIG. 11 is an example diagrammatic view of a computer of FIG. 1 according to one or more example implementations of the disclosure.

Referring also to the example implementation of FIG. 11, there is shown a diagrammatic view of client electronic device 38. While client electronic device 38 is shown in this figure, this is for example purposes only and is not intended to be a limitation of this disclosure, as other configurations are possible. Additionally, any computing device capable of executing, in whole or in part, interactive virtual assistant process 10 may be substituted for client electronic device 38 (in whole or in part) within FIG. 2, examples of which may include but are not limited to computer 12 and/or one or more of client electronic devices 40, 42, 44.

In some implementations, client electronic device 38 may include a processor (e.g., microprocessor 200) configured to, e.g., process data and execute the above-noted code/instruction sets and subroutines. Microprocessor 1100 may be coupled via a storage adaptor to the above-noted storage device(s) (e.g., storage device 30). An I/O controller (e.g., I/O controller 1102) may be configured to couple microprocessor 1100 with various devices (e.g., via wired or wireless connection), such as keyboard 1106, pointing/selecting device (e.g., touchpad, touchscreen, mouse 1108, etc.), custom device (e.g., device 1115), USB ports, and printer ports. A display adaptor (e.g., display adaptor 1110) may be configured to couple display 1112 (e.g., touchscreen monitor(s), plasma, CRT, or LCD monitor(s), etc.) with microprocessor 200, while network controller/adaptor 1114 (e.g., an Ethernet adaptor) may be configured to couple microprocessor 200 to the above-noted network 14 (e.g., the Internet or a local area network).

The terminology used herein is for the purpose of describing particular implementations only and is not intended to be limiting of the disclosure. As used herein, the singular forms "a", "an" and "the" are intended to include the plural forms as well, unless the context clearly indicates otherwise. As used herein, the language "at least one of A, B, and C" (and the like) should be interpreted as covering only A, only B, only C, or any combination of the three, unless the context clearly indicates otherwise. It will be further understood that the terms "comprises" and/or "comprising," when used in this specification, specify the presence of stated features, integers, steps (not necessarily in a particular order), operations, elements, and/or components, but do not preclude the presence or addition of one or more other features, integers, steps (not necessarily in a particular order), operations, elements, components, and/or groups thereof.

The corresponding structures, materials, acts, and equivalents (e.g., of all means or step plus function elements) that may be in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications, variations, substitutions, and any combinations thereof will be apparent to those of ordinary skill in the art without departing from the scope and spirit of the disclosure. The implementation(s) were chosen and described in order to explain the principles of the disclosure and the practical application, and to enable others of ordinary skill in the art to understand the disclosure for various implementation(s) with various modifications and/or any combinations of implementation(s) as are suited to the particular use contemplated.

Having thus described the disclosure of the present application in detail and by reference to implementation(s) thereof, it will be apparent that modifications, variations, and any combinations of implementation(s) (including any modifications, variations, substitutions, and combinations thereof) are possible without departing from the scope of the disclosure defined in the appended claims.

What is claimed is:

1. A computer-implemented method comprising:
    defining, at a computing device, psychometric data for a user;
    selecting an interactive virtual assistant from a plurality of interactive virtual assistants based upon, at least in part, the psychometric data defined for the user;
    providing the selected interactive virtual assistant to the user through the computing device;
    receiving financial transaction data associated with the user;
    prompting the user, via the selected interactive virtual assistant, with an option to rate the financial transaction data by using an emotional annotation; and
    generating an aggregated insight based on emotional annotations associated with members of a combination of cluster groups associated with the user, wherein a cluster group is based on a minimum absolute value distance between the user score and a population median score.

2. The computer-implemented method of claim 1, wherein defining the psychometric data for the user includes:
    providing one or more interactive graphical psychometric tests in a user interface of the computing device.

3. The computer-implemented method of claim 2, wherein the one or more interactive graphical psychometric tests include
    one or more slidable user interface features configured to move along a continuous scale between two end points representative of a first level of a psychometric trait and a second level of the psychometric trait.

4. The computer-implemented method of claim 2, further comprising:
    assigning the user to one or more personality outcomes based upon, at least in part, the one or more interactive graphical psychometric tests provided in the user interface of the computing device.

5. The computer-implemented method of claim 1, wherein the selected interactive virtual assistant is further configured to prompt the user with one or more options via an interactive electronic communication session displayed in a user interface of the computing device.

6. The computer-implemented method of claim 5, wherein prompting the user, via the selected interactive virtual assistant, with the one or more options includes one or more of:
    prompting the user to rate one or more financial transactions;
    prompting the user with one or more financial savings options; and
    prompting the user with one or more financial services options.

7. A computer program product residing on a non-transitory computer readable storage medium having a plurality of instructions stored thereon which, when executed across one or more processors, causes at least a portion of the one or more processors to perform operations comprising:
    defining psychometric data for a user;
    selecting an interactive virtual assistant from a plurality of interactive virtual assistants based upon, at least in part, the psychometric data defined for the user;
    providing the selected interactive virtual assistant to the user through a computing device;
    receiving financial transaction data associated with the user;
    prompting the user, via the selected interactive virtual assistant, with an option to rate the financial transaction data by using an emotional annotation; and
    generating an aggregated insight based on emotional annotations associated with members of a combination of cluster groups associated with the user, wherein a cluster group is based on a minimum absolute value distance between the user score and a population median score.

8. The computer program product of claim 7 wherein defining the psychometric data for the user includes:
    providing one or more interactive graphical psychometric tests in a user interface of the computing device.

9. The computer program product of claim 8 wherein the one or more interactive graphical psychometric tests include one or more slidable user interface features configured to move along a continuous scale between two end points representative of a first level of a psychometric trait and a second level of the psychometric trait.

10. The computer program product of claim 8 further comprising:
    assigning the user to one or more personality outcomes based upon, at least in part, the one or more interactive graphical psychometric tests provided in the user interface of the computing device.

11. The computer program product of claim 7 wherein the selected interactive virtual assistant is further configured to prompt the user with one or more options via an interactive electronic communication session displayed in a user interface of the computing device.

12. The computer program product of claim 11 wherein prompting the user, via the selected interactive virtual assistant, with the one or more options includes one or more of:
   prompting the user to rate one or more financial transactions;
   prompting the user with one or more financial savings options; and
   prompting the user with one or more financial services options.

13. A computing system including one or more processors and one or more memories configured to perform operations comprising:
   defining psychometric data for a user;
   selecting an interactive virtual assistant from a plurality of interactive virtual assistants based upon, at least in part, the psychometric data defined for the user;
   providing the selected interactive virtual assistant to the user through the computing system;
   receiving financial transaction data associated with the user;
   prompting the user, via the selected interactive virtual assistant, with an option to rate the financial transaction data by using an emotional annotation; and
   generating an aggregated insight based on emotional annotations associated with members of a combination of cluster groups associated with the user, wherein a cluster group is based on a minimum absolute value distance between the user score and a population median score.

14. The computing system of claim 13 wherein defining the psychometric data for the user includes:
   providing one or more interactive graphical psychometric tests in a user interface of the computing system.

15. The computing system of claim 14 wherein the one or more interactive graphical psychometric tests include one or more slidable user interface features configured to move along a continuous scale between two end points representative of a first level of a psychometric trait and a second level of the psychometric trait.

16. The computing system of claim 14 further comprising:
   assigning the user to one or more personality outcomes based upon, at least in part, the one or more interactive graphical psychometric tests provided in the user interface of the computing system.

17. The computing system of claim 13 wherein
   the selected interactive virtual assistant is further configured to prompt the user with one or more options via an interactive electronic communication session displayed in a user interface of the computing device.

18. The computing system of claim 17 wherein
   prompting the user, via the selected interactive virtual assistant, with the one or more options includes one or more of:
      prompting the user to rate one or more financial transactions;
      prompting the user with one or more financial savings options; and
      prompting the user with one or more financial services options.

* * * * *